(12) United States Patent
Baldwin et al.

(10) Patent No.: US 8,536,169 B2
(45) Date of Patent: Sep. 17, 2013

(54) COMPOUNDS

(75) Inventors: Ian Robert Baldwin, Stevenage (GB); Kenneth David Down, Stevenage (GB); Paul Faulder, Stevenage (GB); Simon Gaines, Stevenage (GB); Joelle Le, Stevenage (GB); Nigel James Parr, Stevenage (GB); Timothy John Ritchie, Stevenage (GB); Juliet Kay Simpson, Stevenage (GB); Christian Alan Paul Smethurst, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 197 days.

(21) Appl. No.: 12/994,254

(22) PCT Filed: Jun. 3, 2009

(86) PCT No.: PCT/EP2009/056840
§ 371 (c)(1),
(2), (4) Date: Feb. 15, 2011

(87) PCT Pub. No.: WO2009/147189
PCT Pub. Date: Dec. 10, 2009

(65) Prior Publication Data
US 2011/0183973 A1    Jul. 28, 2011

Related U.S. Application Data

(60) Provisional application No. 61/058,957, filed on Jun. 5, 2008.

(51) Int. Cl.
*A61K 31/5377* (2006.01)
*A61K 31/416* (2006.01)
*A61K 31/454* (2006.01)
*A61K 31/4439* (2006.01)
*C07D 401/14* (2006.01)
*C07D 403/04* (2006.01)
*C07D 413/14* (2006.01)

(52) U.S. Cl.
USPC ........ 514/234.5; 514/322; 514/338; 514/406; 544/140; 546/199; 546/275.7; 548/361.1

(58) Field of Classification Search
None
See application file for complete search history.

(56) References Cited

U.S. PATENT DOCUMENTS

| | | | |
|---|---|---|---|
| 8,076,326 B2 | 12/2011 | Haupt et al. | |
| 8,114,868 B2 | 2/2012 | Himmelsbach | |
| 8,138,178 B2 | 3/2012 | Claremon et al. | |
| 8,163,743 B2 | 4/2012 | Baldwin et al. | |
| 8,242,111 B2 | 8/2012 | Claremon et al. | |
| 2004/0009968 A1 | 1/2004 | Binch et al. | |
| 2005/0090529 A1 | 4/2005 | McAlpine et al. | |
| 2005/0288286 A1 | 12/2005 | Flynn et al. | |
| 2006/0135540 A1 | 6/2006 | Lin et al. | |
| 2006/0264433 A1 | 11/2006 | Backes et al. | |
| 2007/0037820 A1 | 2/2007 | Edwards et al. | |
| 2008/0032960 A1 | 2/2008 | Knight et al. | |
| 2008/0200523 A1 | 8/2008 | Murthi et al. | |
| 2009/0203690 A1 | 8/2009 | Akritopoulou-Zanze et al. | |
| 2010/0216792 A1 | 8/2010 | Gorgens et al. | |
| 2010/0256363 A1 | 10/2010 | Xu | |
| 2010/0280014 A1 | 11/2010 | Haupt et al. | |
| 2010/0280029 A1 | 11/2010 | Hamblin et al. | |
| 2010/0280045 A1 | 11/2010 | Hamblin et al. | |
| 2010/0331320 A1 | 12/2010 | Renz et al. | |
| 2011/0009402 A1 | 1/2011 | Himmelsbach | |
| 2011/0015157 A1 | 1/2011 | Claremon et al. | |
| 2011/0021512 A1 | 1/2011 | Claremon et al. | |
| 2011/0067448 A1 | 3/2011 | Matsumoto et al. | |
| 2011/0118246 A1* | 5/2011 | Baldwin et al. ............ | 514/228.5 |
| 2011/0124635 A1 | 5/2011 | Claremon et al. | |
| 2011/0178063 A1* | 7/2011 | Baldwin et al. .......... | 514/211.15 |
| 2011/0183973 A1 | 7/2011 | Baldwin et al. | |
| 2011/0263583 A1 | 10/2011 | Claremon et al. | |
| 2011/0263584 A1 | 10/2011 | Claremon et al. | |
| 2012/0040969 A1 | 2/2012 | Haupt et al. | |
| 2012/0108579 A1 | 5/2012 | Renz et al. | |
| 2012/0129854 A1 | 5/2012 | Mihara et al. | |

(Continued)

FOREIGN PATENT DOCUMENTS

EP    1679308 A1    7/2006
WO    02/067683 A1    9/2002

(Continued)

OTHER PUBLICATIONS

Ameriks, et al., "Small Molecule Inhibitors of Phosphoinositide 3-kinase (PI3K) delta and gamma" Current Topics in Medicinal Chemistry; 2009; vol. 9(8); pp. 738-753.
Finan, et al., "PI3-kinase inhibition: a therapeutic target for respiratory disease"; Biochemical Society Transactions; 2004; vol. 32, part 2; pp. 378-382.
Folkes, et al. The Identification of 2-(1H-indazol-4-yl)-6-(4-methanesulfonyl-piperazin-1-ylmethyl) -4-morpholin-4-yl-thieno [3,2-d] pyrimidine (GDC-0941) as a Potent, Selective, Orally Bioavailable inhibitor of class I PI3 kinase for the treatment of cancer Journal of Medicinal Chemistry; 2008; vol. 51(18); pp. 5522-5532.
Horig, et al., "From bench to clinic and back: Perspective on the 1st IQPC Translational Research Conference"; Journal of Translational Medicine; 2004; vol. 2(44); pp. 1-8.

(Continued)

*Primary Examiner* — Kamal Saeed
(74) *Attorney, Agent, or Firm* — Robert J. Smith

(57) ABSTRACT

The invention is directed to certain novel compounds directed to compounds of formula (I) and salts thereof. The compounds of the invention are inhibitors of PI3-kinase activity.

(I)

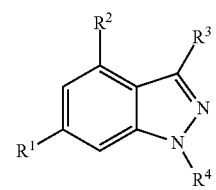

9 Claims, No Drawings

(56) References Cited

U.S. PATENT DOCUMENTS

| | | |
|---|---|---|
| 2012/0178746 A1 | 7/2012 | Claremon et al. |
| 2012/0184549 A1 | 7/2012 | Himmelsbach |
| 2012/0238559 A1 | 9/2012 | Baldwin et al. |
| 2012/0238571 A1 | 9/2012 | Baldwin et al. |
| 2012/0245171 A1* | 9/2012 | Baldwin et al. ............ 514/234.2 |

FOREIGN PATENT DOCUMENTS

| | | |
|---|---|---|
| WO | 02/083111 A2 | 10/2002 |
| WO | 03/000257 A1 | 1/2003 |
| WO | WO 03/051847 | 6/2003 |
| WO | 03/064397 A1 | 8/2003 |
| WO | 2004/002480 A1 | 1/2004 |
| WO | 2004/014370 A2 | 2/2004 |
| WO | 2004/014881 A2 | 2/2004 |
| WO | 2004/014902 A2 | 2/2004 |
| WO | 2005/016245 A1 | 2/2005 |
| WO | 2005/075482 A1 | 8/2005 |
| WO | 2005/077345 A1 | 8/2005 |
| WO | 2005/077368 A2 | 8/2005 |
| WO | 2005/077373 A2 | 8/2005 |
| WO | 2005/082889 A1 | 9/2005 |
| WO | 2006/012226 A2 | 2/2006 |
| WO | 2006/014290 A2 | 2/2006 |
| WO | 2006/055752 A2 | 5/2006 |
| WO | 2006/060535 A2 | 6/2006 |
| WO | 2006/089076 A2 | 8/2006 |
| WO | 2007/017759 A2 | 2/2007 |
| WO | 2007/021573 A1 | 2/2007 |
| WO | 2007/022371 A2 | 2/2007 |
| WO | 2007/105637 A1 | 9/2007 |
| WO | 2007/126841 A2 | 11/2007 |
| WO | 2007/132171 A1 | 11/2007 |
| WO | 2008/016123 A1 | 2/2008 |
| WO | 2008/020229 A2 | 2/2008 |
| WO | 2008/024945 A1 | 2/2008 |
| WO | 2008/037477 A1 | 4/2008 |
| WO | 2008/038136 A2 | 4/2008 |
| WO | 2008/057938 A1 | 5/2008 |
| WO | 2008/090382 A1 | 7/2008 |
| WO | 2009/000832 A1 | 12/2008 |
| WO | 2009/017664 A1 | 2/2009 |
| WO | 2009/134400 A1 | 11/2009 |
| WO | 2009/147187 A1 | 12/2009 |
| WO | 2009/147188 A1 | 12/2009 |
| WO | 2009/147189 A1 | 12/2009 |
| WO | 2009/147190 A1 | 12/2009 |
| WO | 2010/011314 A1 | 1/2010 |
| WO | 2010/043315 A1 | 4/2010 |
| WO | 2010/068287 A2 | 6/2010 |
| WO | 2010/125082 A1 | 11/2010 |
| WO | 2010/125134 A1 | 11/2010 |
| WO | 2010/127237 A2 | 11/2010 |
| WO | 2012/032065 A1 | 3/2012 |
| WO | 2012/032067 A1 | 3/2012 |
| WO | 2012/055846 A1 | 5/2012 |

OTHER PUBLICATIONS

Schafer, et al., "Failure is an option: learning from unsuccessful proof-of-concept trials" Drug Discovery Today; 2008; vol. 13 (21/22); pp. 913-916.

Verheijen, et al., "Phosphatidylinositol 3-kinase (PI3) inhibitors as anticancer drugs" Drugs of the Future, Prous Science; 2007; vol. 32(6); pp. 537-547.

* cited by examiner

COMPOUNDS

This application is a 371 of International Application No. PCT/EP2009/056840, filed 3 Jun. 2009, which claims the benefit of U.S. Provisional Application No. 61/058,957, filed 5 Jun. 2008, which is incorporated herein in its entirety.

FIELD OF THE INVENTION

The present invention is directed to certain novel compounds which are inhibitors of the activity or function of the phosphoinositide 3'OH kinase family (hereinafter PI3-kinases), processes for their preparation, pharmaceutical compositions comprising the compounds, and the use of the compounds or the compositions in the treatment of various disorders. More specifically, the compounds of the invention are inhibitors of the activity or function of, for example, PI3Kδ, PI3Kα, PI3Kβ and/or PI3Kγ. Compounds which are inhibitors of the activity or function of PI3-kinases may be useful in the treatment of disorders such as respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

BACKGROUND OF THE INVENTION

Cellular membranes represent a large store of second messengers that can be enlisted in a variety of signal transduction pathways. In relation to function and regulation of effector enzymes in phospholipids signaling pathways, class I PI3-kinases (e.g. PI3Kdelta) generate second messengers from the membrane phospholipid pools. Class I PI3Ks convert the membrane phospholipid $PI(4,5)P_2$ into $PI(3,4,5)P_3$, which functions as a second messenger. PI and PI(4)P are also substrates of PI3K and can be phosphorylated and converted into PI3P and $PI(3,4)P_2$, respectively. In addition, these phosphoinositides can be converted into other phosphoinositides by 5'-specific and 3'-specific phophatases. Thus, PI3K enzymatic activity results either directly or indirectly in the generation of two 3'-phosphoinositide subtypes which function as second messengers in intracellular signal transduction pathways (Trends Biochem. Sci. 22(7) p. 267-72 (1997) by Vanhaesebroeck et al.; Chem. Rev. 101(8) p. 2365-80 (2001) by Leslie et al.; Annu. Rev. Cell Dev. Biol. 17 p. 615-75 (2001) by Katso et al.; and Cell. Mol. Life. Sci. 59(5) p. 761-79 (2002) by Toker). To date, eight mammalian PI3Ks have been identified, divided into three main classes (I, II, and III) on the basis of sequence homology, structure, binding partners, mode of activation, and substrate preference. In vitro, class I PI3Ks can phosphorylate phosphatidylinositol (PI), phosphatidylinositol-4-phosphate (PI4P), and phosphatidylinositol-4,5-bisphosphate $(PI(4,5)P_2)$ to produce phosphatidylinositol-3-phosphate (PI3P), phosphatidylinositol-3,4-bisphosphate $(PI(3,4)P_2)$, and phosphatidylinositol-3,4,5-trisphosphate $(PI(3,4,5)P_3)$, respectively. Class II PI3Ks can phosphorylate PI and PI4P. Class III PI3Ks can only phosphorylate PI (Vanhaesebroeck et al. (1997), above; Vanhaesebroeck et al., Exp. Cell Res. 253(1) p. 239-54 (1999); and Leslie et al. (2001), above).

Class I PI3K is a heterodimer consisting of a p110 catalytic subunit and a regulatory subunit, and the family is further divided into class Ia and class Ib enzymes on the basis of regulatory partners and mechanism of regulation. Class Ia enzymes consist of three distinct catalytic subunits (p110α, p110β, and p110δ) that dimerise with five distinct regulatory subunits (p85α, p55α, p50α, p85β, and p55γ), with all catalytic subunits being able to interact with all regulatory subunits to form a variety of heterodimers. Class Ia PI3K are generally activated in response to growth factor-stimulation of receptor tyrosine kinases, via interaction of the regulatory subunit SH2 domains with specific phospho-tyrosine residues of the activated receptor or adaptor proteins such as IRS-1. Small GTPases (ras as an example) are also involved in the activation of PI3K in conjunction with receptor tyrosine kinase activation. Both p110α and p110β are constitutively expressed in all cell types, whereas p110δ expression is more restricted to leukocyte populations and some epithelial cells. In contrast, the single Class Ib enzyme consists of a p110γ catalytic subunit that interacts with a p101 regulatory subunit. Furthermore, the Class Ib enzyme is activated in response to G-protein coupled receptor (GPCR) systems and its expression appears to be limited to leukocytes.

Scheme A: Conversion of $PI(4,5)P_2$ to $PI(3,4,5)P_3$

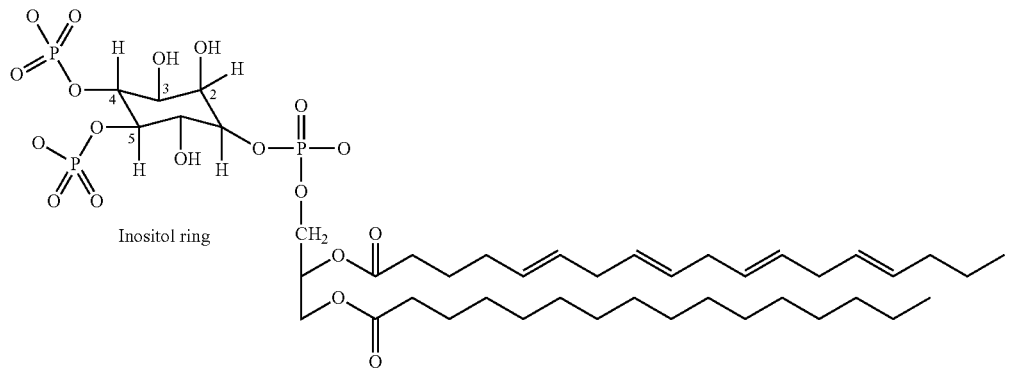

PtdIns(4,5)P$_2$

|PI3K

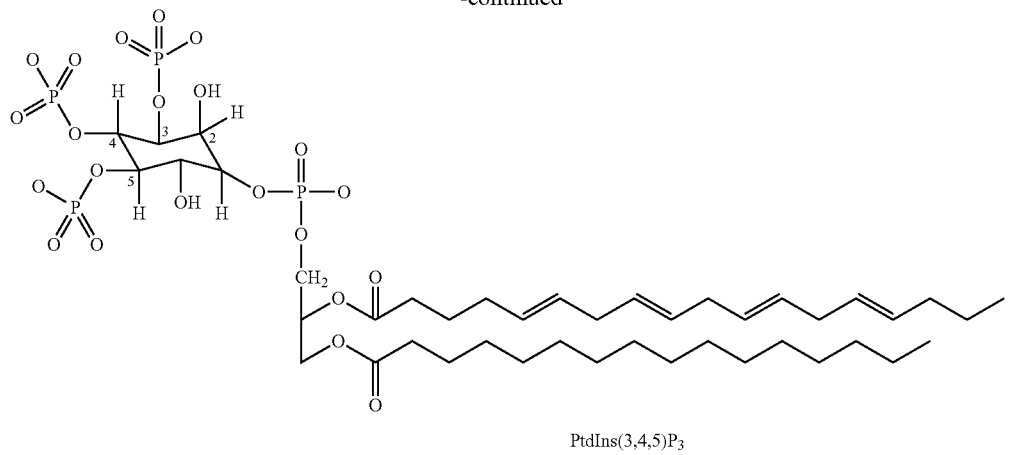

PtdIns(3,4,5)P$_3$

As illustrated in Scheme A above, phosphoinositide 3-kinases (PI3Ks) phosphorylate the hydroxyl of the third carbon of the inositol ring. The phosphorylation of phosphoinositides to generate PtdIns(3,4,5)P$_3$, PtdIns(3,4)P$_2$ and PtdIns(3) P, produces second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (Katso et al. (2001), above; and Mol. Med. Today 6(9) p. 347-57 (2000) by Stein et al.).

The activity of PI3-kinases responsible for generating these phosphorylated signalling products was originally identified as being associated with viral oncoproteins and growth factor receptor tyrosine kinases that phosphorylate phosphatidylinositol (PI) and its phosphorylated derivatives at the 3'-hydroxyl of the inositol ring (Panayotou et al. Trends Cell Biol. 2 p. 358-60 (1992)). However, more recent biochemical studies have revealed that class I PI3-kinases (e.g. class IA isoform PI3Kδ) are dual-specific kinase enzymes, meaning they display both lipid kinase (phosphorylation of phosphoinositides) as well as protein kinase activity, and are capable of phosphorylation of other protein as substrates, including auto-phosphorylation as an intramolecular regulatory mechanism (EMBO J. 18(5) p. 1292-302 (1999) by Vanhaesebroeck et al.). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells.

PI3-kinase activation is believed to be involved in a wide range of cellular responses including cell growth, differentiation, and apoptosis (Parker, Current Biology, 5(6) p. 577-79 (1995); and Yao et al. Science 267(5206) p. 2003-06 (1995)). PI3-kinase appears to be involved in a number of aspects of leukocyte activation. A p85-associated PI3-kinase has been shown to physically associate with the cytoplasmic domain of CD28, which is an important costimulatory molecule for the activation of T-cells in response to antigen (Pagés et al. Nature 369 p. 327-29 (1994); and Rudd, Immunity 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al. Science 251(4991) p. 313-16 (1991)).

PI3Kγ has been identified as a mediator of G beta-gamma-dependent regulation of JNK activity, and G beta-gamma are subunits of heterotrimeric G proteins (Lopez-Ilasaca et al. J. Biol. Chem. 273(5) p. 2505-8 (1998)). Recently, (Laffargue et al. Immunity 16(3) p. 441-51 (2002)) it has been described that PI3Kγ relays inflammatory signals through various G(i)-coupled receptors and is central to mast cell function, stimuli in the context of leukocytes, and immunology including cytokines, chemokines, adenosines, antibodies, integrins, aggregation factors, growth factors, viruses or hormones for example (J. Cell Sci. 114 (Pt 16) p. 2903-10 (2001) by Lawlor et al.; Laffargue et al. (2002), above; and Curr. Opinion Cell Biol. 14(2) p. 203-13 (2002) by Stephens et al.).

Specific inhibitors against individual members of a family of enzymes provide invaluable tools for deciphering functions of each enzyme. Two compounds, LY294002 and wortmannin (hereinafter), have been widely used as PI3-kinase inhibitors. These compounds are non-specific PI3K inhibitors, as they do not distinguish among the four members of Class I PI3-kinases. For example, the IC$_{50}$ values of wortmannin against each of the various Class I PI3-kinases are in the range of 1-10 nM. Similarly, the IC$_{50}$ values for LY294002 against each of these PI3-kinases is about 15-20 μM (Fruman et al. Ann. Rev. Biochem. 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates subsequent cellular response to the extracellular factor. For example, neutrophils respond to the chemokine fMet-Leu-Phe (fMLP) by stimulating PI3K and synthesizing PtdIns (3, 4, 5)P$_3$. This synthesis correlates with activation of the respiratory burst involved in neutrophil destruction of invading microorganisms. Treatment of neutrophils with wortmannin prevents the fMLP-induced respiratory burst response (Thelen et al. Proc. Natl. Acad. Sci. USA 91 p. 4960-64 (1994)). Indeed, these experiments with wortmannin, as well as other experimental evidence, show that PI3K activity in cells of hematopoietic lineage, particularly neutrophils, monocytes, and other types of leukocytes, is involved in many of the non-memory immune response associated with acute and chronic inflammation.

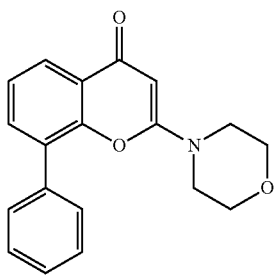

LY294002

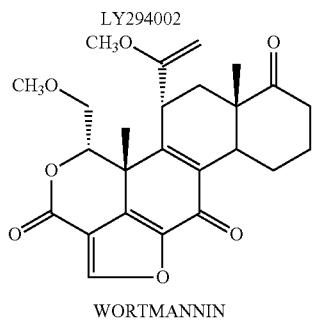

WORTMANNIN

Based on studies using wortmannin, there is evidence that PI3-kinase function is also required for some aspects of leukocyte signaling through G-protein coupled receptors (Thelen et al. (1994), above). Moreover, it has been shown that wortmannin and LY294002 block neutrophil migration and superoxide release.

It is now well understood that deregulation of oncogenes and tumour suppressor genes contributes to the formation of malignant tumours, for example by way of increased cell growth and proliferation or increased cell survival. It is also now known that signaling pathways mediated by the PI3K family have a central role in a number of cell processes including proliferation and survival, and deregulation of these pathways is a causative factor a wide spectrum of human cancers and other diseases (Katso et al. Annual Rev. Cell Dev. Biol. (2001) 17 p. 615-675 and Foster et al. J. Cell Science (2003) 116(15) p. 3037-3040). PI3K effector proteins initiate signalling pathways and networks by translocating to the plasma membrane through a conserved Pleckstrin Homology (PH) domain, which specifically interacts with PtdIns(3,4,5)P3 (Vanhaesebroeck et al. Annu. Rev. Biochem. (2001) 70 p. 535-602). The effector proteins signalling through PtdIns(3,4,5)P3 and PH domains include Serine/Threonine (Ser/Thr) kinases, Tyrosine kinases, Rac or Arf GEFs (Guanine nucleotide exchange factors) and Arf GAPs (GTPase activating proteins).

In B and T cells PI3Ks have an important role through activation of the Tec family of protein tyrosine kinases which include Bruton's tyrosine kinase (BTK) in B cells and Interleukin-2-inducible T-cell kinase (ITK) in T cells. Upon PI3K activation, BTK or ITK translocate to the plasma membrane where they are subsequently phosphorylated by Src kinases. One of the major targets of activated ITK is phospholipase C-gamma (PLCγ1), which hydrolyses PtdIns(4,5)P2 into Ins (3,4,5)P3 and initiates an intracellular increase in calcium levels and diacylglycerol (DAG) which can activate Protein Kinases C in activated T cells.

Unlike the Class IA p110α and p110β, p110δ is expressed in a tissue restricted fashion. Its high expression level in lymphocytes and lymphoid tissues suggests a role in PI3K-mediated signalling in the immune system. The p110δ kinase dead knock-in mice are also viable and their phenotype is restricted to defects in immune signalling (Okkenhaug et al. Science (2002) 297 p. 1031-4). These transgenic mice have offered insight into the function of PI3Kδ in B-cell and T-cell signalling. In particular, p110δ is required for PtdIns(3,4,5) P3 formation downstream of CD28 and/or T cell Receptor (TCR) signalling. A key effect of PI3K signalling downstream of TCR is the activation of Akt, which phosphorylates anti-apoptotic factors as well as various transcription factors for cytokine production. As a consequence, T cells with inactive p110δ have defects in proliferation and Th1 and Th2 cytokine secretion. Activation of T cells through CD28 lowers the threshold for TCR activation by antigen and increases the magnitude and duration of the proliferative response. These effects are mediated by the PI3Kδ-dependent increase in the transcription of a number of genes including IL2, an important T cell growth factor.

Therefore, PI3K inhibitors are anticipated to provide therapeutic benefit via its role in modulating T-cell mediated inflammatory responses associated to respiratory diseases such as asthma, COPD and cystic fibrosis. In addition, there is indication that T-cell directed therapies may provide corticosteroid sparing properties (Alexander et al. Lancet (1992) 339 p. 324-8) suggesting that it may provide a useful therapy either as a standalone or in combination with inhaled or oral glucocorticosteroids in respiratory diseases. A PI3K inhibitor might also be used alongside other conventional therapies such as a long acting beta-agonist (LABA) in asthma.

In the vasculature, PI3Kδ is expressed by endothelial cells and participates in neutrophil trafficking by modulating the proadhesive state of these cells in response to TNFalpha (Puri et al. Blood (2004) 103(9) p. 3448-56). A role for PI3Kδ in TNFalpha-induced signalling of endothelial cells is demonstrated by the pharmacological inhibition of Akt phosphorylation and PDK1 activity. In addition, PI3Kδ is implicated in vascular permeability and airway tissue edema through the VEGF pathway (Lee et al. J. Allergy Clin. Immunol. (2006) 118(2) p. 403-9). These observations suggest additional benefits of PI3Kδ inhibition in asthma by the combined reduction of leukocyte extravasation and vascular permeability associated with asthma. In addition, PI3Kδ activity is required for mast cell function both in vitro and in vivo (Ali et al. Nature (2004) 431 p. 1007-11; and Ali et al. J. Immunol. (2008) 180(4) p. 2538-44) further suggesting that PI3K inhibition should be of therapeutic benefit for allergic indications such asthma, allergic rhinitis and atopic dermatitis.

The role of PI3Kδ in B cell proliferation, antibody secretion, B-cell antigen and IL-4 receptor signalling, B-cell antigen presenting function is also well established Okkenhaug et al. (2002), above; Al-Alwan et al. J. Immunol. (2007) 178(4) p. 2328-35; and Bilancio et al. Blood (2006) 107(2) p. 642-50) and indicates a role in autoimmune diseases such as rheumatoid arthritis or systemic lupus erythematosus. Therefore PI3K inhibitors may also be of benefit for these indications.

Pharmacological inhibition of PI3Kδ inhibits fMLP-dependent neutrophil chemotaxis on an ICAM coated agarose matrix integrin-dependent biased system (Sadhu et al. J. Immunol. (2003) 170(5) p. 2647-54). Inhibition of PI3Kδ regulates neutrophil activation, adhesion and migration without affecting neutrophil mediated phagocytosis and bactericidal activity over *Staphylococcus aureus* (Sadhu et al. Biochem. Biophys. Res. Commun. (2003) 308(4) p. 764-9). Overall, the data suggest that PI3Kδ inhibition should not globally inhibit neutrophil functions required for innate immune defence. PI3Kδ's role in neutrophils offers further scope for treating inflammatory diseases involving tissue remodeling such as COPD or rheumatoid arthritis.

In addition, there is also good evidence that class Ia PI3K enzymes also contribute to tumourigenesis in a wide variety of human cancers, either directly or indirectly (Vivanco and Sawyers, Nature Reviews Cancer (2002) 2(7) p. 489-501). For example, inhibition of PI3Kδ may have a therapeutic role for the treatment of malignant haematological disorders such as acute myeloid leukaemia (Billottet et al. Oncogene (2006)

25(50) p. 6648-59). Moreover, activating mutations within p110a (PIK3CA gene) have been associated with various other tumors such as those of the colon and of the breast and lung (Samuels et al. Science (2004) 304(5670) p. 554).

It has also been shown that PI3K is involved in the establishment of central sensitization in painful inflammatory conditions (Pezet et al. The J. of Neuroscience (2008) 28 (16) p. 4261-4270).

Attempts have been made to prepare compounds which inhibit PI3-kinase activity and a number of such compounds have been disclosed in the art. However, in view of the number of pathological responses which are mediated by PI3-kinases, there remains a continuing need for inhibitors of PI3-kinase which can be used in the treatment of a variety of conditions.

The present inventors have discovered novel compounds which are inhibitors of P13-kinase activity. Compounds which are PI3-kinase inhibitors may be useful in the treatment of disorders associated with inappropriate PI3-kinase activity, for example in the treatment and prevention of disorders mediated by PI3-kinase mechanisms. Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

In one embodiment, compounds of the invention may show selectivity for PI3-kinases over other kinases. For example, the compounds of the invention may show selectivity for PI3-kinases over DNA-dependent protein kinase (DNA-PK).

In one embodiment, compounds of the invention may show selectivity for PI3Kδ over other PI3-kinases. For example, the compounds of the invention may show selectivity for PI3Kδ over PI3Kα and/or PI3Kβ.

SUMMARY OF THE INVENTION

The invention is directed to certain novel compounds. Specifically, the invention is directed to compounds of formula (I)

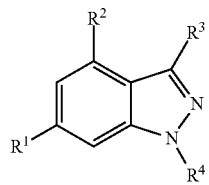

wherein $R^1$, $R^2$, $R^3$ and $R^4$ are as defined below, and salts thereof.

The compounds are inhibitors of PI3-kinase activity. Compounds which are PI3-kinase inhibitors may be useful in the treatment of disorders associated with inappropriate PI3-kinase activity, such as asthma and chronic obstructive pulmonary disease (COPD). Accordingly, the invention is further directed to pharmaceutical compositions comprising a compound of formula (I) or a pharmaceutically acceptable salt thereof. The invention is still further directed to methods of inhibiting PI3-kinase activity and treatment of disorders associated therewith using a compound of formula (I) or a pharmaceutically acceptable salt thereof, or a pharmaceutical composition comprising a compound of formula (I) or a pharmaceutically acceptable salt thereof. The invention is yet further directed towards processes for the preparation for the compounds of the invention.

DETAILED DESCRIPTION OF THE INVENTION

In one embodiment, the invention is directed to compounds of formula (I)

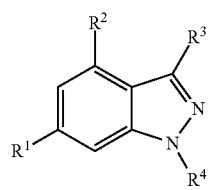

wherein
$R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN;
$R^2$ is —NHCOR$^5$,

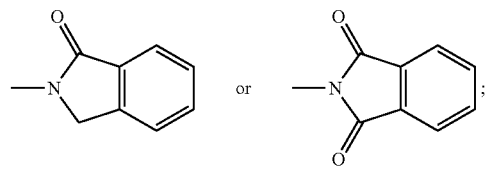

$R^3$ is hydrogen or fluoro;
$R^4$ is hydrogen or methyl;
$R^5$ is
$C_{3-6}$cycloalkyl optionally substituted by phenyl;
5- or 6-membered heterocyclyl wherein the 5- or 6-membered heterocyclyl contains one or two heteroatoms independently selected from oxygen and nitrogen and is optionally substituted by one or two substituents independently selected from oxo, $C_{1-6}$alkyl, —OR$^6$, —COR$^7$, —CO$_2$R$^8$ and —SO$_2$R$^9$;
phenyl optionally substituted by one or two substituents independently selected from $C_{1-6}$alkyl, —OR$^{10}$, halo, —NR$^{11}$R$^{12}$, and phenyl optionally substituted by halo;
—CH$_2$-5- or 6-membered heteroaryl wherein the 5- or 6-membered heteroaryl contains one or two nitrogen atoms and is optionally substituted by $C_{1-6}$alkyl;
pyrazine optionally substituted by —OR$^{13}$; or
9- or 10-membered bicyclic heteroaryl wherein the 9- or 10-membered bicyclic heteroaryl contains one or two nitrogen atoms;
$R^6$, $R^{11}$, $R^{12}$ and $R^{13}$ are each independently hydrogen or $C_{1-6}$alkyl;
$R^7$ and $R^9$ are each independently $C_{1-6}$alkyl;
$R^8$ is hydrogen or —(CH$_2$)$_m$phenyl;

$R^{10}$ is $C_{1-6}$alkyl optionally substituted by from one to three fluoros; and m is 0, 1 or 2;

and salts thereof (hereinafter "compounds of the invention").

In one embodiment, $R^1$ is 9- or 10-membered bicyclic heteroaryl wherein the 9- or 10-membered bicyclic heteroaryl contains from one to three heteroatoms independently selected from oxygen and nitrogen. In a further embodiment, $R^1$ is indolyl.

In one embodiment, $R^2$ is —NHCOR$^5$. In another embodiment, $R^2$ is

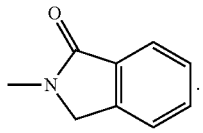

In a further embodiment, $R^2$ is

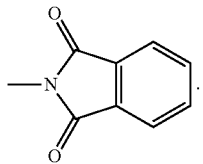

In one embodiment, $R^3$ is hydrogen.

In one embodiment, $R^4$ is hydrogen.

In one embodiment, $R^5$ is $C_{3-6}$cycloalkyl optionally substituted by phenyl. In another embodiment, $R^5$ is cyclopropyl optionally substituted by phenyl. In a further embodiment, $R^5$ is cyclohexyl.

In one embodiment, $R^5$ is 5- or 6-membered heterocyclyl wherein the 5- or 6-membered heterocyclyl contains one or two heteroatoms independently selected from oxygen and nitrogen and is optionally substituted by one or two substituents independently selected from oxo, $C_{1-6}$alkyl, for example $C_{1-4}$alkyl such as methyl or isopropyl, —OR$^6$, —COR$^7$, —CO$_2$R$^8$ and —SO$_2$R$^9$.

In one embodiment, $R^5$ is phenyl optionally substituted by one or two substituents independently selected from $C_{1-6}$alkyl, for example $C_{1-4}$alkyl such as methyl, —OR$^{10}$, halo, —NR$^{11}$R$^{12}$, and phenyl optionally substituted by halo.

In one embodiment, $R^5$ is —CH$_2$-5- or 6-membered heteroaryl wherein the 5- or 6-membered heteroaryl contains one or two nitrogen atoms and is optionally substituted by $C_{1-6}$alkyl. In another embodiment, $R^5$ is —CH$_2$-pyrazolyl optionally substituted by $C_{1-6}$alkyl, for example $C_{1-4}$alkyl such as methyl. In a further embodiment, $R^5$ is —CH$_2$-pyridinyl.

In one embodiment, $R^5$ is pyrazine optionally substituted by —OR$^{13}$.

In one embodiment, $R^5$ is 9- or 10-membered bicyclic heteroaryl wherein the 9- or 10-membered bicyclic heteroaryl contains one or two nitrogen atoms. In a further embodiment, $R^5$ is indolyl, benzimidazolyl, pyrazolopyridinyl, or isoquinolinyl.

In one embodiment, $R^6$ is hydrogen.

In one embodiment, $R^7$ is $C_{1-4}$alkyl such as methyl.

In one embodiment, $R^8$ is —(CH$_2$)$_m$phenyl.

In one embodiment, $R^9$ is $C_{1-4}$alkyl such as methyl.

In one embodiment, $R^{10}$ is $C_{1-4}$alkyl such as methyl or ethyl, optionally substituted by one or two fluoros.

In one embodiment, $R^{11}$ and $R^{12}$ are each hydrogen. In a further embodiment, $R^{11}$ and $R^{12}$ are each independently $C_{1-4}$alkyl such as methyl.

In one embodiment, $R^{13}$ is $C_{1-4}$alkyl such as methyl.

In one embodiment, m is 1.

It is to be understood that the present invention covers all combinations of substituent groups described hereinabove.

Compounds of the invention include the compounds of Examples 1 to 37 and salts thereof.

In one embodiment, the compound of the invention is:

N-[6-(1H-indol-4-yl)-1H-indazol-4-yl]benzamide;
2-fluoro-N-[6-(1H-indol-4-yl)-1H-indazol-4-yl]benzamide;
2,3-difluoro-N-[6-(1H-indol-4-yl)-1H-indazol-4-yl]benzamide;
2,5-difluoro-N-[6-(1H-indol-4-yl)-1H-indazol-4-yl]benzamide;
N-[6-(1H-indol-4-yl)-1H-indazol-4-yl]-2-methylbenzamide;
2'-chloro-N-[6-(1H-indol-4-yl)-1H-indazol-4-yl]-2-biphenylcarboxamide;
N-[6-(1H-indol-4-yl)-1H-indazol-4-yl]-1-isoquinolinecarboxamide;
2,4-difluoro-N-[6-(1H-indol-4-yl)-1H-indazol-4-yl]benzamide;
2,6-difluoro-N-[6-(1H-indol-4-yl)-1H-indazol-4-yl]benzamide;
N-[6-(1H-indol-4-yl)-1H-indazol-4-yl]-2-(methyloxy)benzamide;
2-[(difluoromethyl)oxy]-N-[6-(1H-indol-4-yl)-1H-indazol-4-yl]benzamide;
N-[6-(1H-Indol-4-yl)-1H-indazol-4-yl]pyrazolo[1,5-a]pyridine-2-carboxamide;
N-[6-(1H-indol-4-yl)-1H-indazol-4-yl]-6-(methyloxy)-2-pyrazinecarboxamide;
N-[6-(1H-indol-4-yl)-1H-indazol-4-yl]-1H-benzimidazole-2-carboxamide;
N-[6-(1H-indol-4-yl)-1H-indazol-4-yl]-1H-indole-2-carboxamide;
N-[6-(1H-indol-4-yl)-1H-indazol-4-yl]-4-methyl-2-(methyloxy)benzamide;
N-[6-(1H-indol-4-yl)-1H-indazol-4-yl]-5-methyl-2-(methyloxy)benzamide;
N-[6-(1H-indol-4-yl)-1H-indazol-4-yl]-2-(3-methyl-1H-pyrazol-1-yl)acetamide;
N-[6-(1H-indol-4-yl)-1H-indazol-4-yl]-3-methyl-2-(methyloxy)benzamide;
2-(ethyloxy)-N-[6-(1H-indol-4-yl)-1H-indazol-4-yl]benzamide;
4-acetyl-N-[6-(1H-indol-4-yl)-1H-indazol-4-yl]-2-morpholinecarboxamide;
N-[6-(1H-indol-4-yl)-1H-indazol-4-yl]-2-(2-pyridinyl)acetamide;
2-[6-(1H-indol-4-yl)-1H-indazol-4-yl]-1H-isoindole-1,3(2H)-dione;
2-[6-(1H-indol-4-yl)-1H-indazol-4-yl]-2,3-dihydro-1H-isoindol-1-one;
N-[6-(1H-indol-4-yl)-1H-indazol-4-yl]-3-methylbenzamide;
N-[6-(1H-indol-4-yl)-1H-indazol-4-yl]-4-methyl-2-morpholinecarboxamide;
1-acetyl-N-[6-(1H-indol-4-yl)-1H-indazol-4-yl]-4-piperidinecarboxamide;
N-[6-(1H-indol-4-yl)-1H-indazol-4-yl]-1-methyl-4-piperidinecarboxamide;
N-[6-(1H-indol-4-yl)-1H-indazol-4-yl]-1-(methylsulfonyl)-4-piperidinecarboxamide;

N-[6-(1H-indol-4-yl)-1H-indazol-4-yl]-5-oxo-3-pyrrolidinecarboxamide;
N-[6-(1H-indol-4-yl)-1H-indazol-4-yl]-1-(1-methylethyl)-5-oxo-3-pyrrolidinecarboxamide;
N-[6-(1H-indol-4-yl)-1H-indazol-4-yl]cyclopropanecarboxamide;
3-(dimethylamino)-N-[6-(1H-indol-4-yl)-1H-indazol-4-yl]benzamide;
4-amino-N-[6-(1H-indol-4-yl)-1H-indazol-4-yl]benzamide;
(1R,2R)—N-[6-(1H-indol-4-yl)-1H-indazol-4-yl]-2-phenylcyclopropanecarboxamide;
N-[6-(1H-indol-4-yl)-1H-indazol-4-yl]cyclohexanecarboxamide;
phenylmethyl 3-hydroxy-4-({[6-(1H-indol-4-yl)-1H-indazol-4-yl]amino}carbonyl)-1-pyrrolidinecarboxylate; or
a salt thereof.

TERMS AND DEFINITIONS

"Alkyl" refers to a saturated hydrocarbon chain having the specified number of member atoms. For example, $C_{1-6}$alkyl refers to an alkyl group having from 1 to 6 member atoms. Similarly, $C_{1-4}$alkyl refers to an alkyl group having from 1 to 4 member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl. In one embodiment, alkyl is methyl. In another embodiment, alkyl is ethyl. In a further embodiment, alkyl is isopropyl.

"Cycloalkyl" refers to a saturated hydrocarbon ring having the specified number of member atoms. Cycloalkyl groups are monocyclic ring systems. For example, $C_{3-6}$cycloalkyl refers to a cycloalkyl group having from 3 to 6 member atoms. In one embodiment, the cycloalkyl groups have 3 or 4 member atoms. In a further embodiment, the cycloalkyl groups have 5 or 6 member atoms. Cycloalkyl groups may be optionally substituted with one or more substituents if so defined herein. It will be appreciated that the substituent may be at any position on the ring, including the carbon atom which is the point of attachment to the rest of the molecule. Cycloalkyl includes cyclopropyl, cyclobutyl, cyclopentyl, and cyclohexyl. In one embodiment, cycloalkyl is cyclopropyl. In a further embodiment, cycloalkyl is cyclohexyl.

"Enantiomerically enriched" refers to products whose enantiomeric excess is greater than zero. For example, enantiomerically enriched refers to products whose enantiomeric excess is greater than 50% ee, greater than 75% ee, and greater than 90% ee.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" (or "half-lives") refers to the time required for half of a quantity of a substance to be converted to another chemically distinct species in vitro or in vivo.

"Halo" refers to the halogen radical fluoro, chloro, bromo, or iodo. In one embodiment, the halogen radical is fluoro, chloro or bromo.

"Heteroaryl", unless otherwise defined, refers to an aromatic ring containing from 1 to 3 heteroatoms as member atoms in the ring. Heteroaryl groups containing more than one heteroatom may contain different heteroatoms. Heteroaryl groups may be optionally substituted with one or more substituents if so defined herein. The heteroaryl groups herein are monocyclic ring systems or are fused bicyclic ring systems. Monocyclic heteroaryl rings have 5 or 6 member atoms. Bicyclic heteroaryl rings have 9 or 10 member atoms. Monocyclic heteroaryl includes pyrrolyl, pyridinyl, pyrazolyl, imidazolyl, pyrimidinyl, pyridazinyl and pyrazinyl. In one embodiment, monocyclic heteroaryl is pyrazolyl or pyridinyl. Bicyclic heteroaryl includes indolyl, isoindolyl, indolizinyl, benzofuranyl, isobenzofuranyl, indazolyl, purinyl, benzimidazolyl, pyrrolopyridinyl, pyrazolopyridinyl, pyrrolopyrimidinyl, quinolyl, isoquinolinyl, quinoxalinyl, quinazolinyl, cinnolinyl, benzopyranyl, benzoxazolyl, furopyridinyl and naphthridinyl. In one embodiment, bicyclic heteroaryl is indolyl, benzimidazolyl, pyrazolopyridinyl, or isoquinolinyl. In a further embodiment, bicyclic heteroaryl is indolyl.

"Heteroatom" refers to a nitrogen, sulphur, or oxygen atom.

"Heterocyclyl" refers to a saturated or unsaturated ring containing 1 or 2 heteroatoms as member atoms in the ring. However, heterocyclyl rings are not aromatic. Heterocyclyl groups containing more than one heteroatom may contain different heteroatoms. The heterocyclyl groups herein are monocyclic ring systems having 5 or 6 member atoms. Heterocyclyl groups may be optionally substituted with one or more substituents if so defined herein. In certain embodiments, heterocyclyl is saturated. In other embodiments, heterocyclyl is unsaturated but not aromatic. Heterocyclyl includes pyrrolidinyl, pyrazolidinyl, oxazolidinyl, piperidinyl, piperazinyl and morpholinyl. In one embodiment, heterocyclyl is pyrrolidinyl, piperidinyl or morpholinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as heteroaryl, may be unsubstituted or substituted with one or more substituents if so defined herein.

"Substituted" in reference to a group indicates that a hydrogen atom attached to a member atom within a group is replaced. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination). In certain embodiments, a single atom may be substituted with more than one substituent as long as such substitution is in accordance with the permitted valence of the atom. Suitable substituents are defined herein for each substituted or optionally substituted group.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

DCM Dichloromethane
DIPEA Diisopropylethylamine
DMF N,N-Dimethylformamide
DMSO Dimethylsulfoxide
g Grams
h or hr hour(s)
HATU O-(7-azabenzotriazol-1-yl)-N,N,N',N'-tetramethyluronium hexafluorophosphate
HPLC High performance liquid chromatography
LCMS Liquid chromatography mass spectroscopy
M Molar
MeCN Acetonitrile
MeOH Methanol
mg Milligrams
mins Minutes
ml or mL Milliliters
mmol Millimoles
PS polymer supported
Pd(dppf)Cl$_2$ [1,1'-bis(diphenylphosphino)ferrocene]dichloropalladium(II)
R$_t$ or Rt Retention time
RT Room temperature
SCX Strong Cation Exchange
SPE Solid Phase Extraction
TFA Trifluoroacetic acid
THF Tetrahydrofuran
HPLC Ultra high performance liquid chromatography
UV Ultraviolet All references to brine are to a saturated aqueous solution of NaCl.

Included within the scope of the "compounds of the invention" are all solvates (including hydrates), complexes, polymorphs, prodrugs, radiolabelled derivatives, stereoisomers and optical isomers of the compounds of formula (I) and salts thereof.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and EtOAc, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs". The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making or recrystallising the compound. For example, changes in temperature, pressure, or solvent may result in polymorphs. In addition, one polymorph may spontaneously convert to another polymorph under certain conditions.

The invention also includes isotopically-labelled compounds, which are identical to the compounds of formula (I) and salts thereof, but for the fact that one or more atoms are replaced by an atom having an atomic mass or mass number different from the atomic mass or mass number most commonly found in nature. Examples of isotopes that can be incorporated into the compounds of the invention include isotopes of hydrogen, carbon, nitrogen, oxygen and fluorine, such as 3H, 11C, 14C and 18F.

The compounds according to formula (I) may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in formula (I), or in any chemical structure illustrated herein, is not specified the structure is intended to encompass any stereoisomer and all mixtures thereof. Thus, compounds according to formula (I) containing one or more chiral center may be used as racemic mixtures, enantiomerically enriched mixtures, or as enantiomerically pure individual stereoisomers.

Individual stereoisomers of a compound according to formula (I) which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to formula (I) may also contain centers of geometric asymmetry. Where the stereochemistry of a center of geometric asymmetry present in formula (I), or in any chemical structure illustrated herein, is not specified, the structure is intended to encompass the trans geometric isomer, the cis geometric isomer, and all mixtures thereof. Likewise, all tautomeric forms are also included in formula (I) whether such tautomers exist in equilibrium or predominately in one form.

It is to be understood that the references herein to compounds of formula (I) and salts thereof covers the compounds of formula (I) as free acids or free bases, or as salts thereof, for example as pharmaceutically acceptable salts thereof. Thus, in one embodiment, the invention is directed to compounds of formula (I) as the free acid or free base. In another embodiment, the invention is directed to compounds of formula (I) and salts thereof. In a further embodiment, the invention is directed to compounds of formula (I) and pharmaceutically acceptable salts thereof.

The skilled artisan will appreciate that pharmaceutically acceptable salts of the compounds according to formula (I) may be prepared. Indeed, in certain embodiments of the invention, pharmaceutically acceptable salts of the compounds according to formula (I) may be preferred over the respective free base or free acid because such salts impart greater stability or solubility to the molecule thereby facilitating formulation into a dosage form. Accordingly, the invention is further directed to compounds of formula (I) and pharmaceutically acceptable salts thereof.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

Salts and solvates having non-pharmaceutically acceptable counter-ions or associated solvents are within the scope of the present invention, for example, for use as intermediates in the preparation of other compounds of formula (I) and their pharmaceutically acceptable salts. Thus one embodiment of the invention embraces compounds of formula (I) and salts thereof.

In certain embodiments, compounds according to formula (I) may contain an acidic functional group. Suitable pharmaceutically-acceptable salts include salts of such acidic functional groups. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, TEA, ethylenediamine, ethanolamine, diethanolamine, and cyclohexylamine.

In certain embodiments, compounds according to formula (I) may contain a basic functional group and are therefore capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, naphthoate, hydroxynaphthoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

Compound Preparation

The compounds of the invention may be made by a variety of methods, including standard chemistry. Any previously defined variable will continue to have the previously defined meaning unless otherwise indicated. Illustrative general synthetic methods are set out below and then specific compounds of the invention are prepared in the Examples section.

Process a

Compounds of formula (I) wherein $R^1$, $R^2$, $R^3$ and $R^4$ are as defined above, and salts thereof, may be prepared from compounds of formula (II)

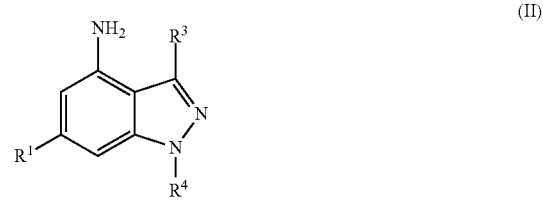

wherein $R^1$, $R^3$ and $R^4$ are as defined above, by a process comprising (i) treatment with an acid of formula $R^2COOH$, wherein $R^2$ is as defined above, or (ii) treatment with an acid chloride of formula $R^2COCl$, wherein $R^2$ is as defined above.

Suitable conditions for (i) include stirring in a suitable solvent such as N,N-dimethylformamide, at a suitable temperature such as room temperature, for example about 20° C., in the presence of a coupling reagent such as O-(7-azabenzotriazol-1-yl)-N,N,N'N'-tetramethyluronium hexafluorophosphate, and in the presence of a suitable base such as N,N-diisopropylethylamine. Alternatively, (ii) may be carried out by treatment with an acylating agent such as an acid chloride, in a suitable solvent such as dichloromethane, in the presence of a suitable base such as N,N-diisopropylethylamine, and at a suitable temperature such as room temperature, for example about 20° C.

Compounds of formula (II) wherein $R^1$, $R^3$ and $R^4$ are as defined above and $R^3$ is H, may be prepared from the compound of formula (III) (which is commercially available)

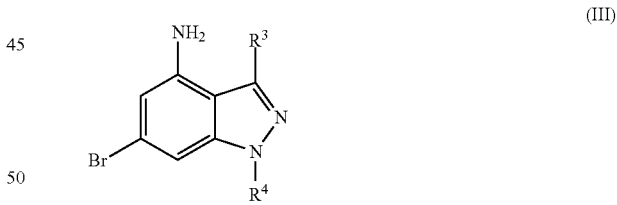

wherein $R^3$ and $R^4$ are H, by treatment with a suitable boronic acid or boronate ester such as 4-(4,4,5,5-tetramethyl-1,3,2-dioxaborolan-2-yl)-1H-indole (commercially available), in the presence of a suitable palladium catalyst such as 1,1'-bis(diphenylphosphino)ferrocene palladium dichloride, in a suitable solvent such as a mixture of 1,4-dioxane and water, in the presence of a suitable base such as sodium carbonate, and at a suitable temperature such as 60-200° C., for example about 115° C. Alternatively, this process may be carried out under microwave irradiation, at a suitable temperature such as 60-200° C., for example about 150° C.

Process b

Compounds of formula (I) wherein $R^1$, $R^2$ and $R^3$ are as defined above and $R^4$ is H, and salts thereof, may be prepared from compounds of formula (IV)

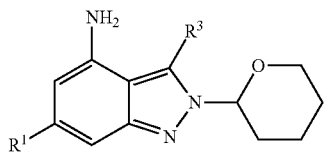

(IV)

wherein $R^1$ and $R^3$ are as defined above, by a process comprising treatment either with (i) a suitable acid of formula $R^2COOH$, wherein $R^2$ is as defined above, followed by deprotection using a suitable acid, or (ii) an acid chloride of formula $R^2COCl$, wherein $R^2$ is as defined above, followed by deprotection by a suitable acid. Suitable conditions for (i) include stirring an acid such as for example, 2-methyl-1,3-thiazole-4-carboxylic acid (commercially available), in a suitable solvent such as N,N-dimethylformamide, at a suitable temperature such as room temperature, for example about 20° C., in the presence of a coupling reagent such as O-(7-azabenzotriazol-1-yl)-N,N,N'N'-tetramethyluronium hexafluorophosphate, and in the presence of a suitable base such as N,N-diisopropylethylamine, followed by treatment with a suitable acid such as macroporus toluenesulphonic acid. Alternatively, (ii) may be carried out by acylation with a suitable acylating agent such as an acid chloride, in a suitable solvent such as dichloromethane, in the presence of a suitable base such as N,N-diisopropylamine, and at a suitable temperature such as room temperature, for example about 20° C., followed by treatment with a suitable acid such as macroporus toluenesulphonic acid.

Compounds of formula (IV) wherein $R^1$ and $R^3$ are as defined above, may be prepared from compounds of formula (V)

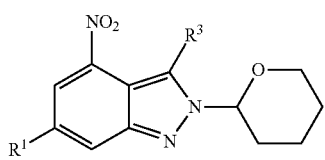

(V)

wherein $R^1$ and $R^3$ are as described above, by hydrogenation in a Thales H-Cube®, in the presence of a suitable catalyst such as palladium on carbon, in a suitable solvent such as ethyl acetate, at a suitable temperature such as 20-40° C., for example about 30° C., and at a suitable pressure such as 1-50 bar, for example about 30 bar.

Compounds of formula (V) wherein $R^1$ and $R^3$ are as defined above, may be prepared from compounds of formula (VI)

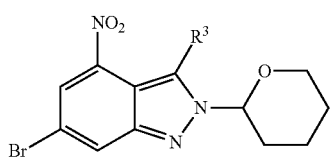

(VI)

wherein $R^3$ is as defined above, by treatment with a suitable boronic acid such as [4-(tetrahydro-2H-pyran-2-yloxy)phenyl]boronic acid, under microwave irradiation, in the presence of a suitable palladium catalyst such as 1,1'-bis(diphenylphosphino)ferrocene palladium dichloride, in a suitable solvent such as isopropanol, in the presence of a suitable base such as aqueous saturated sodium hydrogencarbonate, and at a suitable temperature such as 60-180° C., for example about 150° C.

Compounds of formula (VI) wherein $R^3$ is hydrogen, may be prepared from the compound of formula (VII) (which is commercially available)

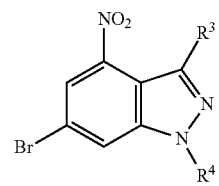

(VII)

wherein $R^3$ and $R^4$ are H, by treatment with 3,4-dihydro-2H-pyran, with a suitable acid catalyst such as pyridinium p-toluene sulfonate, in a suitable solvent such as dichloromethane, and at a suitable temperature, such as reflux temperature.

Process c

Compounds of formula (I) wherein $R^1$, $R^2$ and $R^3$ are as defined above and $R^4$ is H, may be prepared from compounds of formula (II) as described above by condensation with a suitable anhydride such as benzofuran-1,3-dione, under microwave irradiation, in a suitable solvent such as N,N-dimethylformamide, and at a suitable temperature such as between 60-200° C., for example about 150° C. Alternatively, process c may be carried out by treatment of compounds of formula (II) as described above wherein $R^4$ is H, by condensation with a suitable dialdehyde, such as 1,2-benzene dicarbaldehyde, in a suitable solvent, such as ethyl acetate, with a suitable acid catalyst such as acetic acid, at a suitable, temperature such as between 20-50° C., for example room temperature.

Compounds of formula (II), wherein $R^1$ and $R^3$ are as defined above and $R^4$ is H, may be prepared from the compound of formula (III) as described above.

Thus, in one embodiment, the invention provides a process for preparing a compound of the invention comprising:

a) reacting a compound of formula (II)

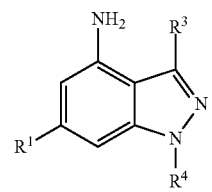

(II)

wherein $R^1$, $R^3$ and $R^4$ are as defined above, with (i) an acid of formula $R^2COOH$, wherein $R^2$ is as defined above, or (ii) with an acid chloride of formula $R^2COCl$, wherein $R^2$ is as defined above, b) for a compound of formula (I) wherein $R^1$, $R^2$ and $R^3$ are as defined above and $R^4$ is H, or a salt thereof, reacting a compound of formula (IV)

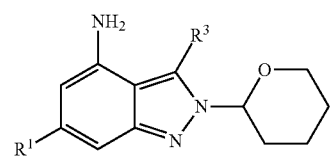

(IV)

wherein $R^1$ and $R^3$ are as defined above, with (i) a suitable acid of formula $R^2COOH$, wherein $R^2$ is as defined above, followed by deprotection using a suitable acid, or (ii) an acid chloride of formula $R^2COCl$, wherein $R^2$ is as defined above, followed by deprotection by a suitable acid, or c) for a compound of formula (I) wherein $R^1$, $R^2$ and $R^3$ are as defined above and $R^4$ is H, or a salt thereof, condensing a compound of formula (II) as described above with a suitable anhydride.

Methods of Use

The compounds of the invention are inhibitors of PI3-kinase activity. Compounds which are PI3-kinase inhibitors may be useful in the treatment of disorders wherein the underlying pathology is (at least in part) attributable to inappropriate PI3-kinase activity, such as asthma and chronic obstructive pulmonary disease (COPD). "Inappropriate PI3-kinase activity" refers to any PI3-kinase activity that deviates from the normal PI3-kinase activity expected in a particular patient. Inappropriate PI3-kinase may take the form of, for instance, an abnormal increase in activity, or an aberration in the timing and or control of PI3-kinase activity. Such inappropriate activity may result then, for example, from overexpression or mutation of the protein kinase leading to inappropriate or uncontrolled activation. Accordingly, in another aspect the invention is directed to methods of treating such disorders.

Such disorders include respiratory diseases including asthma and chronic obstructive pulmonary disease (COPD); allergic diseases including allergic rhinitis and atopic dermatitis; autoimmune diseases including rheumatoid arthritis and multiple sclerosis; inflammatory disorders including inflammatory bowel disease; cardiovascular diseases including thrombosis and atherosclerosis; hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain including pain associated with rheumatoid arthritis or osteoarthritis, back pain, general inflammatory pain, post hepatic neuralgia, diabetic neuropathy, inflammatory neuropathic pain (trama), trigeminal neuralgia and central pain.

The methods of treatment of the invention comprise administering a safe and effective amount of a compound of formula (I) or a pharmaceutically acceptable salt thereof to a patient in need thereof. Individual embodiments of the invention include methods of treating any one of the above-mentioned disorders by administering a safe and effective amount of a compound of formula (I) or a pharmaceutically acceptable salt thereof to a patient in need thereof.

As used herein, "treat" in reference to a disorder means: (1) to ameliorate or prevent the disorder or one or more of the biological manifestations of the disorder, (2) to interfere with (a) one or more points in the biological cascade that leads to or is responsible for the disorder or (b) one or more of the biological manifestations of the disorder, (3) to alleviate one or more of the symptoms or effects associated with the disorder, or (4) to slow the progression of the disorder or one or more of the biological manifestations of the disorder.

As indicated above, "treatment" of a disorder includes prevention of the disorder. The skilled artisan will appreciate that "prevention" is not an absolute term. In medicine, "prevention" is understood to refer to the prophylactic administration of a drug to substantially diminish the likelihood or severity of a disorder or biological manifestation thereof, or to delay the onset of such disorder or biological manifestation thereof.

As used herein, "safe and effective amount" in reference to a compound of formula (I) or a pharmaceutically acceptable salt thereof or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the disorder being treated; the severity of the disorder being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human (including adults and children) or other animal. In one embodiment, "patient" refers to a human.

The compounds of formula (I) or pharmaceutically acceptable salts thereof may be administered by any suitable route of administration, including both systemic administration and topical administration. Systemic administration includes oral administration, parenteral administration, transdermal administration and rectal administration. Parenteral administration refers to routes of administration other than enteral or transdermal, and is typically by injection or infusion. Parenteral administration includes intravenous, intramuscular, and subcutaneous injection or infusion. Topical administration includes application to the skin as well as intraocular, otic, intravaginal, inhaled and intranasal administration. Inhalation refers to administration into the patient's lungs whether inhaled through the mouth or through the nasal passages. In one embodiment, the compounds of formula (I) or pharmaceutically acceptable salts thereof may be administered orally. In another embodiment, the compounds of formula (I) or pharmaceutically acceptable salts thereof may be administered by inhalation. In a further embodiment, the compounds of formula (I) or pharmaceutically acceptable salts thereof may be administered intranasally. Preferably, the compounds of formula (I) or pharmaceutically acceptable salts thereof are administered by inhalation.

The compounds of formula (I) or pharmaceutically acceptable salts thereof may be administered once or according to a dosing regimen wherein a number of doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for a compound of formula (I) or a pharmaceutically acceptable salt thereof depend on the pharmacokinetic properties of that compound, such as absorption, distribution, and half-life, which can be determined by the skilled artisan. In addition, suitable dosing regimens, including the duration such regimens are administered, for a compound of formula (I) or a pharmaceutically acceptable salt thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical daily dosages for oral administration range from 0.001 mg to 50 mg per kg of total body weight, for example from 1 mg to 10 mg per kg of total body weight. For example, daily dosages for oral administration may be from 0.5 mg to 2 g per patient, such as 10 mg to 1 g per patient.

Additionally, the compounds of formula (I) may be administered as prodrugs. As used herein, a "prodrug" of a compound of formula (I) is a functional derivative of the compound which, upon administration to a patient, eventually liberates the compound of formula (I) in vivo. Administration of a compound of formula (I) as a prodrug may enable the skilled artisan to do one or more of the following: (a) modify the onset of the activity of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleavable in vivo. Such modifications, which include the preparation of phosphates, amides, esters, thioesters, carbonates, and carbamates, are well known to those skilled in the art.

The invention thus provides a method of treating a disorder mediated by inappropriate PI3-kinase activity comprising administering a safe and effective amount of a compound of formula (I) or a pharmaceutically acceptable salt thereof to a patient in need thereof.

In one embodiment, the disorder mediated by inappropriate PI3-kinase activity is selected from the group consisting of respiratory diseases (including asthma and chronic obstructive pulmonary disease (COPD)); allergic diseases (including allergic rhinitis and atopic dermatitis); autoimmune diseases (including rheumatoid arthritis and multiple sclerosis); inflammatory disorders (including inflammatory bowel disease); cardiovascular diseases (including thrombosis and atherosclerosis); hematologic malignancies; cystic fibrosis; neurodegenerative diseases; pancreatitis; multiorgan failure; kidney diseases; platelet aggregation; cancer; sperm motility; transplantation rejection; graft rejection; lung injuries; and pain (including pain associated with rheumatoid arthritis or osteoarthritis, back pain, general inflammatory pain, post hepatic neuralgia, diabetic neuropathy, inflammatory neuropathic pain (trama), trigeminal neuralgia and central pain).

In one embodiment, the disorder mediated by inappropriate PI3-kinase activity is a respiratory disease. In a further embodiment, the disorder mediated by inappropriate PI3-kinase activity is asthma. In a further embodiment, the disorder mediated by inappropriate PI3-kinase activity is chronic obstructive pulmonary disease (COPD).

In one embodiment, the disorder mediated by inappropriate PI3-kinase activity is pain.

In one embodiment, the invention provides a compound of formula (I) or a pharmaceutically acceptable salt thereof for use in medical therapy. In another embodiment, the invention provides a compound of formula (I) or a pharmaceutically acceptable salt thereof for use in the treatment of a disorder mediated by inappropriate PI3-kinase activity. In a further embodiment, the invention provides the use of a compound of formula (I) or a pharmaceutically acceptable salt thereof in the manufacture of a medicament for use in the treatment of a disorder mediated by inappropriate PI3-kinase activity.

Compositions

The compounds of formula (I) and pharmaceutically acceptable salts thereof will normally, but not necessarily, be formulated into pharmaceutical compositions prior to administration to a patient. Accordingly, in another aspect the invention is directed to pharmaceutical compositions comprising a compound of formula (I) or a pharmaceutically acceptable salt thereof and one or more pharmaceutically-acceptable excipients.

The pharmaceutical compositions of the invention may be prepared and packaged in bulk form wherein a safe and effective amount of a compound of formula (I) or a pharmaceutically acceptable salt thereof can be extracted and then given to the patient such as with powders or syrups. Alternatively, the pharmaceutical compositions of the invention may be prepared and packaged in unit dosage form wherein each physically discrete unit contains a compound of formula (I) or a pharmaceutically acceptable salt thereof. When prepared in unit dosage form, the pharmaceutical compositions of the invention typically may contain, for example, from 0.5 mg to 1 g, or from 1 mg to 700 mg, or from 5 mg to 100 mg of a compound of formula (I) or a pharmaceutically acceptable salt thereof.

The pharmaceutical compositions of the invention typically contain one compound of formula (I) or a pharmaceutically acceptable salt thereof.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of formula (I) or a pharmaceutically acceptable salt thereof when administered to a patient and interactions which would result in pharmaceutical compositions that are not pharmaceutically acceptable are avoided. In addition, each excipient must of course be pharmaceutically-acceptable eg of sufficiently high purity.

The compound of formula (I) or a pharmaceutically acceptable salt thereof and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of formula (I) or pharmaceutically acceptable salts thereof once administered to the patient from one organ, or portion of the body, to another organ, or portion of the body. Certain pharmaceutically acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other excipients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Accordingly, in another aspect the invention is directed to process for the preparation of a pharmaceutical composition comprising a compound of formula (I) or a pharmaceutically acceptable salt thereof and one or more pharmaceutically-acceptable excipients which comprises mixing the ingredients. A pharmaceutical composition comprising a compound of formula (I) or a pharmaceutically acceptable salt thereof may be prepared by, for example, admixture at ambient temperature and atmospheric pressure.

In one embodiment, the compounds of formula (I) or pharmaceutically acceptable salts thereof will be formulated for oral administration. In another embodiment, the compounds of formula (I) or pharmaceutically acceptable salts thereof will be formulated for inhaled administration. In a further embodiment, the compounds of formula (I) or pharmaceutically acceptable salts thereof will be formulated for intranasal administration. Preferably, the compounds of formula (I) or pharmaceutically acceptable salts thereof will be formulated for inhaled administration.

In one aspect, the invention is directed to a solid oral dosage form such as a tablet or capsule comprising a safe and effective amount of a compound of formula (I) or a pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of formula (I) or pharmaceutically acceptable salts thereof may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of formula (I) or pharmaceutically acceptable salts thereof may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of formula (I) or a pharmaceutically acceptable salt thereof. Syrups can be prepared by dissolving the compound of formula (I) or a pharmaceutically acceptable salt thereof in a suitably flavored aqueous solution, while elixirs are prepared through the use of a non-toxic alcoholic vehicle. Suspensions can be formulated by dispersing the compound of formula (I) or a pharmaceutically acceptable salt thereof in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

In another aspect, the invention is directed to a dosage form adapted for administration to a patient by inhalation, for example, as a dry powder, an aerosol, a suspension, or a solution composition. Preferably, the invention is directed to a dry powder composition adapted for inhalation comprising compound of formula (I) or a pharmaceutically acceptable salt thereof.

Dry powder compositions for delivery to the lung by inhalation typically comprise a compound of formula (I) or a pharmaceutically acceptable salt thereof as a finely divided powder together with one or more pharmaceutically-acceptable excipients as finely divided powders. Pharmaceutically-acceptable excipients particularly suited for use in dry powders are known to those skilled in the art and include lactose, starch, mannitol, and mono-, di-, and polysaccharides. The finely divided powder may be prepared by, for example, micronisation and milling. Generally, the size-reduced (eg micronised) compound can be defined by a $D_{50}$ value of about 1 to about 10 microns (for example as measured using laser diffraction).

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 µg-10 mg of the compound of formula (I) or a pharmaceutically acceptable salt thereof.

Aerosols may be formed by suspending or dissolving a compound of formula (I) or a pharmaceutically acceptable salt thereof in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (I) or a pharmaceutically acceptable salt thereof will typically be administered to a patient via a metered dose inhaler (MDI). Such devices are known to those skilled in the art.

The aerosol may contain additional pharmaceutically-acceptable excipients typically used with MDIs such as surfactants, lubricants, cosolvents and other excipients to improve the physical stability of the formulation, to improve valve performance, to improve solubility, or to improve taste.

There is thus provided as a further aspect of the invention a pharmaceutical aerosol formulation comprising a compound of formula (I) or a pharmaceutically acceptable salt thereof and a fluorocarbon or hydrogen-containing chlorofluorocarbon as propellant, optionally in combination with a surfactant and/or a cosolvent.

According to another aspect of the invention, there is provided a pharmaceutical aerosol formulation wherein the propellant is selected from 1,1,1,2-tetrafluoroethane, 1,1,1,2,3,3,3-heptafluoro-n-propane and mixtures thereof.

The formulations of the invention may be buffered by the addition of suitable buffering agents.

Capsules and cartridges for use in an inhaler or insufflator, of for example gelatine, may be formulated containing a powder mix for inhalation of a compound of formula (I) or a pharmaceutically acceptable salt thereof and a suitable powder base such as lactose or starch. Each capsule or cartridge may generally contain from 20 µg to 10 mg of the compound of formula (I) or pharmaceutically acceptable salt thereof. Alternatively, the compound of formula (I) or pharmaceutically acceptable salt thereof may be presented without excipients such as lactose.

The proportion of the active compound of formula (I) or pharmaceutically acceptable salt thereof in the local compositions according to the invention depends on the precise type of formulation to be prepared but will generally be within the range of from 0.001 to 10% by weight. Generally, for most types of preparations, the proportion used will be within the range of from 0.005 to 1%, for example from 0.01 to 0.5%. However, in powders for inhalation or insufflation the proportion used will normally be within the range of from 0.1 to 5%.

Aerosol formulations are preferably arranged so that each metered dose or "puff" of aerosol contains from 20 µg to 10 mg, preferably from 20 µg to 2000 µg, more preferably from about 20 µg to 500 µg of a compound of formula (I). Administration may be once daily or several times daily, for example 2, 3, 4 or 8 times, giving for example 1, 2 or 3 doses each time. The overall daily dose with an aerosol will be within the range from 100 µg to 10 mg, preferably from 200 µg to 2000 µg. The overall daily dose and the metered dose delivered by capsules and cartridges in an inhaler or insufflator will generally be double that delivered with aerosol formulations.

In the case of suspension aerosol formulations, the particle size of the particulate (e.g., micronised) drug should be such as to permit inhalation of substantially all the drug into the lungs upon administration of the aerosol formulation and will thus be less than 100 microns, desirably less than 20 microns, and in particular in the range of from 1 to 10 microns, such as from 1 to 5 microns, more preferably from 2 to 3 microns.

The formulations of the invention may be prepared by dispersal or dissolution of the medicament and a compound of formula (I) or a pharmaceutically acceptable salt thereof in the selected propellant in an appropriate container, for example, with the aid of sonication or a high-shear mixer. The process is desirably carried out under controlled humidity conditions.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The stability of the suspension aerosol formulations according to the invention may be measured by conventional techniques, for example, by measuring flocculation size distribution using a back light scattering instrument or by measuring particle size distribution by cascade impaction or by the "twin impinger" analytical process. As used herein reference to the "twin impinger" assay means "Determination of the deposition of the emitted dose in pressurised inhalations using apparatus A" as defined in British Pharmacopaeia 1988, pages A204-207, Appendix XVII C. Such techniques enable the "respirable fraction" of the aerosol formulations to be calculated. One method used to calculate the "respirable fraction" is by reference to "fine particle fraction" which is the amount of active ingredient collected in the lower impingement chamber per actuation expressed as a percentage of the total amount of active ingredient delivered per actuation using the twin impinger method described above.

The term "metered dose inhaler" or MDI means a unit comprising a can, a secured cap covering the can and a formulation metering valve situated in the cap. MDI system includes a suitable channelling device. Suitable channelling devices comprise for example, a valve actuator and a cylindrical or cone-like passage through which medicament may be delivered from the filled canister via the metering valve to the nose or mouth of a patient such as a mouthpiece actuator.

MDI canisters generally comprise a container capable of withstanding the vapour pressure of the propellant used such as a plastic or plastic-coated glass bottle or preferably a metal can, for example, aluminium or an alloy thereof which may optionally be anodised, lacquer-coated and/or plastic-coated (for example incorporated herein by reference WO96/32099 wherein part or all of the internal surfaces are coated with one or more fluorocarbon polymers optionally in combination with one or more non-fluorocarbon polymers), which container is closed with a metering valve. The cap may be secured onto the can via ultrasonic welding, screw fitting or crimping. MDIs taught herein may be prepared by methods of the art (e.g. see Byron, above and WO96/32099). Preferably the canister is fitted with a cap assembly, wherein a drug-metering valve is situated in the cap, and said cap is crimped in place.

In one embodiment of the invention the metallic internal surface of the can is coated with a fluoropolymer, more preferably blended with a non-fluoropolymer. In another embodiment of the invention the metallic internal surface of the can is coated with a polymer blend of polytetrafluoroethylene (PTFE) and polyethersulfone (PES). In a further embodiment of the invention the whole of the metallic internal surface of the can is coated with a polymer blend of polytetrafluoroethylene (PTFE) and polyethersulfone (PES).

The metering valves are designed to deliver a metered amount of the formulation per actuation and incorporate a gasket to prevent leakage of propellant through the valve. The gasket may comprise any suitable elastomeric material such as, for example, low density polyethylene, chlorobutyl, bromobutyl, EPDM, black and white butadiene-acrylonitrile rubbers, butyl rubber and neoprene. Suitable valves are commercially available from manufacturers well known in the aerosol industry, for example, from Valois, France (e.g. DF10, DF30, DF60), Bespak plc, UK (e.g. BK300, BK357) and 3M-Neotechnic Ltd, UK (e.g. Spraymiser™).

In various embodiments, the MDIs may also be used in conjunction with other structures such as, without limitation, overwrap packages for storing and containing the MDIs, including those described in U.S. Pat. Nos. 6,119,853; 6,179,118; 6,315,112; 6,352,152; 6,390,291; and 6,679,374, as well as dose counter units such as, but not limited to, those described in U.S. Pat. Nos. 6,360,739 and 6,431,168.

Conventional bulk manufacturing methods and machinery well known to those skilled in the art of pharmaceutical aerosol manufacture may be employed for the preparation of large-scale batches for the commercial production of filled canisters. Thus, for example, in one bulk manufacturing method for preparing suspension aerosol formulations a metering valve is crimped onto an aluminium can to form an empty canister. The particulate medicament is added to a charge vessel and liquefied propellant together with the optional excipients is pressure filled through the charge vessel into a manufacturing vessel. The drug suspension is mixed before recirculation to a filling machine and an aliquot of the drug suspension is then filled through the metering valve into the canister. In one example of a bulk manufacturing method for preparing solution aerosol formulations, a metering valve is crimped onto an aluminium can to form an empty canister. The liquefied propellant together with the optional excipients and the dissolved medicament is pressure filled through the charge vessel into a manufacturing vessel.

In an alternative process, an aliquot of the liquefied formulation is added to an open canister under conditions which are sufficiently cold to ensure the formulation does not vaporise, and then a metering valve crimped onto the canister.

Typically, in batches prepared for pharmaceutical use, each filled canister is check-weighed, coded with a batch number and packed into a tray for storage before release testing.

Suspensions and solutions comprising a compound of formula (I) or a pharmaceutically acceptable salt thereof may also be administered to a patient via a nebulizer. The solvent or suspension agent utilized for nebulization may be any pharmaceutically-acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically-acceptable excipients may be added to the suspension or solution. The compound of formula (I) or pharmaceutically acceptable salt thereof may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of formula (I) or pharmaceutically acceptable salt thereof. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

In a further aspect, the invention is directed to a dosage form adapted for intranasal administration.

Formulations for administration to the nose may include pressurised aerosol formulations and aqueous formulations administered to the nose by pressurised pump. Formulations which are non-pressurised and adapted to be administered topically to the nasal cavity are of particular interest. Suitable formulations contain water as the diluent or carrier for this purpose. Aqueous formulations for administration to the lung or nose may be provided with conventional excipients such as buffering agents, tonicity modifying agents and the like. Aqueous formulations may also be administered to the nose by nebulisation.

The compounds of formula (I) or pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO05/044354, the entire content of which is hereby incorporated herein by reference. The dispenser has a housing which houses a fluid discharge device having a compression pump mounted on a container for containing a fluid formulation. The housing has at least one finger-operable side lever which is movable inwardly with respect to the housing to cam the container upwardly in the housing to cause the pump to compress and pump a metered dose of the formulation out of a pump stem through a nasal nozzle of the housing. In one embodiment, the fluid dispenser is of the general type illustrated in FIGS. 30-40 of WO05/044354.

Pharmaceutical compositions adapted for intranasal administration wherein the carrier is a solid include a coarse powder having a particle size for example in the range 20 to 500 microns which is administered by rapid inhalation through the nasal passage from a container of the powder held close up to the nose. Suitable compositions wherein the carrier is a liquid, for administration as a nasal spray or as nasal drops, include aqueous or oil solutions of the compound of formula (I) or a pharmaceutically acceptable salt thereof.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as arachis oil or castor oil, or a solvent such as polyethylene glycol. Thickening agents and gelling agents which may be used according to the nature of the base include soft paraffin, aluminium stearate, cetostearyl alcohol, polyethylene glycols, woolfat, beeswax, carboxypolymethylene and cellulose derivatives, and/or glyceryl monostearate and/or non-ionic emulsifying agents.

Lotions may be formulated with an aqueous or oily base and will in general also contain one or more emulsifying agents, stabilising agents, dispersing agents, suspending agents or thickening agents.

Powders for external application may be formed with the aid of any suitable powder base, for example, talc, lactose or starch. Drops may be formulated with an aqueous or non-aqueous base also comprising one or more dispersing agents, solubilising agents, suspending agents or preservatives.

Topical preparations may be administered by one or more applications per day to the affected area; over skin areas occlusive dressings may advantageously be used. Continuous or prolonged delivery may be achieved by an adhesive reservoir system.

For treatments of the eye or other external tissues, for example mouth and skin, the compositions may be applied as a topical ointment or cream. When formulated in an ointment, the compound of formula (I) or a pharmaceutically acceptable salt thereof may be employed with either a paraffinic or a water-miscible ointment base. Alternatively, the compound of formula (I) or pharmaceutically acceptable salt thereof may be formulated in a cream with an oil-in-water cream base or a water-in-oil base.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

The compound and pharmaceutical formulations according to the invention may be used in combination with or include one or more other therapeutic agents, for example selected from anti-inflammatory agents, anticholinergic agents (particularly an $M_1/M_2/M_3$ receptor antagonist), $\beta_2$-adrenoreceptor agonists, antiinfective agents, such as antibiotics or antivirals, or antihistamines. The invention thus provides, in a further aspect, a combination comprising a compound of formula (I) or a pharmaceutically acceptable salt thereof together with one or more other therapeutically active agents, for example selected from an anti-inflammatory agent, such as a corticosteroid or an NSAID, an anticholinergic agent, a $\beta_2$-adrenoreceptor agonist, an antiinfective agent, such as an antibiotic or an antiviral, or an antihistamine. One embodiment of the invention encompasses combinations comprising a compound of formula (I) or a pharmaceutically acceptable salt thereof together with a $\beta_2$-adrenoreceptor agonist, and/or an anticholinergic, and/or a PDE-4 inhibitor, and/or an antihistamine.

Certain compounds of the invention may show selectivity for PI3Kδ over other PI3-kinases. The invention thus provides, in a further aspect, a combination comprising a compound of formula (I) or a pharmaceutically acceptable salt thereof which is selective for PI3Kδ together with a compound or pharmaceutically acceptable salt thereof which is selective for another PI3-kinase, for example PI3Kγ.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimise the activity and/or stability and/or physical characteristics, such as solubility, of the therapeutic ingredient. It will be clear also that, where appropriate, the therapeutic ingredients may be used in optically pure form.

In one embodiment, the invention encompasses a combination comprising a compound of formula (I) or a pharmaceutically acceptable salt thereof together with a $\beta_2$-adrenoreceptor agonist.

Examples of $\beta_2$-adrenoreceptor agonists include salmeterol (which may be a racemate or a single enantiomer such as the R-enantiomer), salbutamol (which may be a racemate or a single enantiomer such as the R-enantiomer), formoterol (which may be a racemate or a single duastereomer such as the R,R-diastereomer), salmefamol, fenoterol carmoterol, etanterol, naminterol, clenbuterol, pirbuterol, flerbuterol, reproterol, bambuterol, indacaterol, terbutaline and salts thereof, for example the xinafoate (1-hydroxy-2-naphthalenecarboxylate) salt of salmeterol, the sulphate salt or free base of salbutamol or the fumarate salt of formoterol. In one embodiment, long-acting $\beta_2$-adrenoreceptor agonists, for example, compounds which provide effective bronchodilation for about 12 hrs or longer, are preferred.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Examples of β₂-adrenoreceptor agonists include:

3-(4-{[6-({(2R)-2-hydroxy-2-[4-hydroxy-3-(hydroxymethyl)phenyl]ethyl}amino) hexyl]oxy}butyl)benzenesulfonamide;

3-(3-{[7-({(2R)-2-hydroxy-2-[4-hydroxy-3-hydroxymethyl)phenyl]ethyl}-amino) heptyl]oxy}propyl)benzenesulfonamide;

4-{(1R)-2-[(6-{2-[(2,6-dichlorobenzyl) oxy]ethoxy}hexyl) amino]-1-hydroxyethyl}-2-(hydroxymethyl)phenol;

4-{(1R)-2-[(6-{4-[3-(cyclopentylsulfonyl)phenyl] butoxy}hexyl)amino]-1-hydroxyethyl}-2-(hydroxymethyl)phenol;

N-[2-hydroxyl-5-[(1R)-1-hydroxy-2-[[2-4-[[(2R)-2-hydroxy-2-phenylethyl]amino]phenyl]ethyl]amino]ethyl] phenyl]formamide;

N-2{2-[4-(3-phenyl-4-methoxyphenyl)aminophenyl]ethyl}-2-hydroxy-2-(8-hydroxy-2(1H)-quinolinon-5-yl)ethylamine; and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one.

The β₂-adrenoreceptor agonist may be in the form of a salt formed with a pharmaceutically acceptable acid selected from sulphuric, hydrochloric, fumaric, hydroxynaphthoic (for example 1- or 3-hydroxy-2-naphthoic), cinnamic, substituted cinnamic, triphenylacetic, sulphamic, sulphanilic, naphthaleneacrylic, benzoic, 4-methoxybenzoic, 2- or 4-hydroxybenzoic, 4-chlorobenzoic and 4-phenylbenzoic acid.

Suitable anti-inflammatory agents include corticosteroids. Suitable corticosteroids which may be used in combination with the compounds of formula (I) or pharmaceutically acceptable salts thereof are those oral and inhaled corticosteroids and their pro-drugs which have anti-inflammatory activity. Examples include methyl prednisolone, prednisolone, dexamethasone, fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester (fluticasone furoate), 6α,9α-difluoro-11β-hydroxy-16α-methyl-3-oxo-17α-propionyloxy-androsta-1,4-diene-17β-carbothioic acid S-(2-oxo-tetrahydro-furan-35-yl) ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester, beclomethasone esters (for example the 17-propionate ester or the 17,21-dipropionate ester), budesonide, flunisolide, mometasone esters (for example mometasone furoate), triamcinolone acetonide, rofleponide, ciclesonide (16α,17-[[(R)-cyclohexylmethylene]bis(oxy)]-11β,21-dihydroxy-pregna-1,4-diene-3,20-dione), butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester and 6α,9α-difluoro-11β-hydroxy-16α-methyl-17α-(1-methylcyclopropylcarbonyl)oxy-3-oxo-androsta-1,4-diene-17β-carbothioic acid S-fluoromethyl ester. In one embodiment the corticosteroid is 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Examples of corticosteroids may include those described in WO2002/088167, WO2002/100879, WO2002/12265, WO2002/12266, WO2005/005451, WO2005/005452, WO2006/072599 and WO2006/072600.

Non-steroidal compounds having glucocorticoid agonism that may possess selectivity for transrepression over transactivation and that may be useful in combination therapy include those covered in the following patents: WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651 and WO03/08277. Further non-steroidal compounds are covered in: WO2006/000401, WO2006/000398 and WO2006/015870.

Examples of anti-inflammatory agents include non-steroidal anti-inflammatory drugs (NSAID's).

Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors. An iNOS (inducible nitric oxide synthase inhibitor) is preferably for oral administration. Examples of iNOS inhibitors include those disclosed in WO93/13055, WO98/30537, WO02/50021, WO95/34534 and WO99/62875. Examples of CCR3 inhibitors include those disclosed in WO02/26722.

In one embodiment, the invention provides the use of the compounds of formula (I) in combination with a phosphodiesterase 4 (PDE4) inhibitor, especially in the case of a formulation adapted for inhalation. The PDE4-specific inhibitor useful in this aspect of the invention may be any compound that is known to inhibit the PDE4 enzyme or which is discovered to act as a PDE4 inhibitor, and which are only PDE4 inhibitors, not compounds which inhibit other members of the PDE family, such as PDE3 and PDE5, as well as PDE4.

Compounds include cis-4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]. Also, cis-4-cyano-4-[3-(cyclopentyloxy)-4-methoxyphenyl]cyclohexane-1-carboxylic acid (also known as cilomilast) and its salts, esters, pro-drugs or physical forms, which is described in U.S. Pat. No. 5,552,438 issued 3 Sep. 1996; this patent and the compounds it discloses are incorporated herein in full by reference.

Other compounds include AWD-12-281 from Elbion (Hofgen, N. et al. 15th EFMC Int Symp Med Chem (September 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in the published international patent application WO04/024728 (Glaxo Group Ltd), WO04/056823 (Glaxo Group Ltd) and WO04/103998 (Glaxo Group Ltd) (e.g. Example 399 or 544 disclosed therein). Further compounds are also disclosed in WO2005/058892, WO2005/090348, WO2005/090353, and WO2005/090354, all in the name of Glaxo Group Limited.

Examples of anticholinergic agents are those compounds that act as antagonists at the muscarinic receptors, in particular those compounds which are antagonists of the $M_1$ or $M_3$ receptors, dual antagonists of the $M_1/M_3$ or $M_2/M_3$, receptors or pan-antagonists of the $M_1/M_2/M_3$ receptors. Exemplary compounds for administration via inhalation include ipratropium (for example, as the bromide, CAS 22254-24-6, sold under the name Atrovent), oxitropium (for example, as the bromide, CAS 30286-75-0) and tiotropium (for example, as the bromide, CAS136310-93-5, sold under the name Spiriva). Also of interest are revatropate (for example, as the hydrobromide, CAS 262586-79-8) and LAS-34273 which is disclosed in WO01/04118. Exemplary compounds for oral administration include pirenzepine (CAS 28797-61-7), darifenacin (CAS133099-04-4, or CAS133099-07-7 for the hydrobromide sold under the name Enablex), oxybutynin (CAS 5633-20-5, sold under the name Ditropan), terodiline (CAS15793-40-5), tolterodine (CAS124937-51-5, or CAS124937-52-6 for the tartrate, sold under the name Detrol), otilonium (for example, as the bromide, CAS 26095-59-0, sold under the name Spasmomen), trospium chloride (CAS10405-02-4) and solifenacin (CAS 242478-37-1, or CAS 242478-38-2 for the succinate also known as YM-905 and sold under the name Vesicare).

Additional compounds are disclosed in WO 2005/037280, WO 2005/046586 and WO 2005/104745, incorporated herein by reference. The present combinations include, but are not limited to:
(3-endo)-3-(2,2-di-2-thienylethenyl)-8,8-dimethyl-8-azoniabicyclo[3.2.1]octane iodide;
(3-endo)-3-(2-cyano-2,2-diphenylethyl)-8,8-dimethyl-8-azoniabicyclo[3.2.1]octane bromide;
4-[hydroxy(diphenyl)methyl]-1-{2-[(phenylmethyl)oxy]ethyl}-1-azoniabicyclo[2.2.2]octane bromide; and
(1R,5S)-3-(2-cyano-2,2-diphenylethyl)-8-methyl-8-{2-[(phenylmethyl)oxy]ethyl}-8-azoniabicyclo[3.2.1]octane bromide.

Other anticholinergic agents include compounds which are disclosed in U.S. patent application 60/487,981 including, for example:
(3-endo)-3-(2,2-di-2-thienylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane bromide;
(3-endo)-3-(2,2-diphenylethenyl)-8,8-dimethyl-8-azoniabicyclo[3.2.1]octane 4-methylbenzenesulfonate;
(3-endo)-8,8-dimethyl-3-[2-phenyl-2-(2-thienyl)ethenyl]-8-azoniabicyclo[3.2.1]octane bromide; and/or
(3-endo)-8,8-dimethyl-3-[2-phenyl-2-(2-pyridinyl)ethenyl]-8-azoniabicyclo[3.2.1]octane bromide.

Further anticholinergic agents include compounds which are disclosed in U.S. patent application 60/511,009 including, for example:
(endo)-3-(2-methoxy-2,2-di-thiophen-2-yl-ethyl)-8,8-dimethyl-8-azonia-bicyclo[3.2.1]octane iodide;
3-((endo)-8-methyl-8-aza-bicyclo[3.2.1]oct-3-yl)-2,2-diphenyl-propionitrile;
(endo)-8-methyl-3-(2,2,2-triphenyl-ethyl)-8-aza-bicyclo[3.2.1]octane;
3-((endo)-8-methyl-8-aza-bicyclo[3.2.1]oct-3-yl)-2,2-diphenyl-propionamide;
3-((endo)-8-methyl-8-aza-bicyclo[3.2.1]oct-3-yl)-2,2-diphenyl-propionic acid;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
3-((endo)-8-methyl-8-aza-bicyclo[3.2.1]oct-3-yl)-2,2-diphenyl-propan-1-ol;
N-benzyl-3-((endo)-8-methyl-8-aza-bicyclo[3.2.1]oct-3-yl)-2,2-diphenyl-propionamide;
(endo)-3-(2-carbamoyl-2,2-diphenyl-ethyl)-8,8-dimethyl-8-azonia-bicyclo[3.2.1]octane iodide;
1-benzyl-3-[3-((endo)-8-methyl-8-aza-bicyclo[3.2.1]oct-3-yl)-2,2-diphenyl-propyl]-urea;
1-ethyl-3-[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-acetamide;
N-[3-((endo)-8-methyl-8-aza-bicyclo[3.2.1]oct-3-yl)-2,2-diphenyl-propyl]-benzamide;
3-((endo)-8-methyl-8-aza-bicyclo[3.2.1]oct-3-yl)-2,2-di-thiophen-2-yl-propionitrile;
(endo)-3-(2-cyano-2,2-di-thiophen-2-yl-ethyl)-8,8-dimethyl-8-azonia-bicyclo[3.2.1]octane iodide;
N-[3-((endo)-8-methyl-8-aza-bicyclo[3.2.1]oct-3-yl)-2,2-diphenyl-propyl]-benzenesulfonamide;
[3-((endo)-8-methyl-8-aza-bicyclo[3.2.1]oct-3-yl)-2,2-diphenyl-propyl]-urea;
N-[3-((endo)-8-methyl-8-aza-bicyclo[3.2.1]oct-3-yl)-2,2-diphenyl-propyl]-methanesulfonamide; and/or
(endo)-3-{2,2-diphenyl-3-[(1-phenyl-methanoyl)-amino]-propyl}-8,8-dimethyl-8-azonia-bicyclo[3.2.1]octane bromide.

Further compounds include:
(endo)-3-(2-methoxy-2,2-di-thiophen-2-yl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane iodide;
(endo)-3-(2-cyano-2,2-diphenyl-ethyl)-8,8-dimethyl-8-azonia-bicyclo[3.2.1]octane bromide;
(endo)-3-(2-carbamoyl-2,2-diphenyl-ethyl)-8,8-dimethyl-8-azonia-bicyclo[3.2.1]octane iodide;
(endo)-3-(2-cyano-2,2-di-thiophen-2-yl-ethyl)-8,8-dimethyl-8-azonia-bicyclo[3.2.1]octane iodide; and/or
(endo)-3-{2,2-diphenyl-3-[(1-phenyl-methanoyl)-amino]-propyl}-8,8-dimethyl-8-azonia-bicyclo[3.2.1]octane bromide.

In one embodiment the invention provides a combination comprising a compound of formula (I) or a pharmaceutically acceptable salt thereof together with an H1 antagonist. Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine. In a further embodiment the invention provides a combination comprising a compound of formula (I) or a pharmaceutically acceptable salt thereof together with an H3 antagonist (and/or inverse agonist). Examples of H3 antagonists include, for example, those compounds disclosed in WO2004/035556 and in WO2006/045416. Other histamine receptor antagonists which may be used in combination with the compounds of the present invention include antagonists (and/or inverse agonists) of the H4 receptor, for example, the compounds disclosed in Jablonowski et al., J. Med. Chem. 46:3957-3960 (2003).

The invention thus provides, in a further aspect, a combination comprising a compound of formula (I) or a pharmaceutically acceptable salt thereof together with a PDE4 inhibitor.

The invention thus provides, in a further aspect, a combination comprising a compound of formula (I) or a pharmaceutically acceptable salt thereof together with a $\beta_2$-adrenoreceptor agonist.

The invention thus provides, in a further aspect, a combination comprising a compound of formula (I) or a pharmaceutically acceptable salt thereof together with a corticosteroid.

The invention thus provides, in a further aspect, a combination comprising a compound of formula (I) or a pharmaceutically acceptable salt thereof together with a non-steroidal GR agonist.

The invention thus provides, in a further aspect, a combination comprising a compound of formula (I) or a pharmaceutically acceptable salt thereof together with an anticholinergic.

The invention thus provides, in a further aspect, a combination comprising a compound of formula (I) or a pharmaceutically acceptable salt thereof together with an antihistamine.

The invention thus provides, in a further aspect, a combination comprising a compound of formula (I) or a pharmaceutically acceptable salt thereof together with a PDE4 inhibitor and a $\beta_2$-adrenoreceptor agonist.

The invention thus provides, in a further aspect, a combination comprising a compound of formula (I) or a pharmaceutically acceptable salt thereof together with an anticholinergic and a PDE-4 inhibitor.

In a preferred aspect, the invention provides a combination comprising a compound of formula (I) or a pharmaceutically acceptable salt thereof together with a corticosteroid.

In a further preferred aspect, the invention provides a combination comprising a compound of formula (I) or a pharmaceutically acceptable salt thereof together with a $\beta_2$-adrenoreceptor agonist.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of formula (I) or a pharmaceutically acceptable salt thereof together with another therapeutically active agent.

The invention thus provides, in a further aspect, a pharmaceutical composition comprising a combination of a compound of formula (I) or a pharmaceutically acceptable salt thereof together with a PDE4 inhibitor.

The invention thus provides, in a further aspect, a pharmaceutical composition comprising a combination of a compound of formula (I) or a pharmaceutically acceptable salt thereof together with a $\beta_2$-adrenoreceptor agonist.

The invention thus provides, in a further aspect, a pharmaceutical composition comprising a combination of a compound of formula (I) or a pharmaceutically acceptable salt thereof together with a corticosteroid.

The invention thus provides, in a further aspect, a pharmaceutical composition comprising a combination of a compound of formula (I) or a pharmaceutically acceptable salt thereof together with a non-steroidal GR agonist.

The invention thus provides, in a further aspect, a pharmaceutical composition comprising a combination of a compound of formula (I) or a pharmaceutically acceptable salt thereof together with an anticholinergic.

The invention thus provides, in a further aspect, a pharmaceutical composition comprising a combination of a compound of formula (I) or a pharmaceutically acceptable salt thereof together with an antihistamine.

The invention thus provides, in a further aspect, a pharmaceutical composition comprising a combination of a compound of formula (I) or a pharmaceutically acceptable salt thereof together with a PDE4 inhibitor and a $\beta_2$-adrenoreceptor agonist.

The invention thus provides, in a further aspect, a pharmaceutical composition comprising a combination of a compound of formula (I) or a pharmaceutically acceptable salt thereof together with an anticholinergic and a PDE4 inhibitor.

In a preferred aspect, the invention provides a pharmaceutical composition comprising a combination of a compound of formula (I) or a pharmaceutically acceptable salt thereof together with a corticosteroid.

In a further preferred aspect, the invention provides a pharmaceutical composition comprising a combination of a compound of formula (I) or a pharmaceutically acceptable salt thereof together with a $\beta_2$-adrenoreceptor agonist.

The invention will now be illustrated by way of the following non-limiting examples.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

General Methods

Liquid Chromatography Mass Spectroscopy (LCMS) Methods

LCMS analysis has been carried out using one of the methods listed below.

LCMS Method A

Waters ZQ mass spectrometer operating in positive ion electrospray mode, mass range 100-1000 amu.

UV wavelength: 215-330 nm

Column: 3.3 cm×4.6 mm ID, 3 μm ABZ+PLUS
Flow Rate: 3 ml/min
Injection Volume: 5 μl
Solvent A: 95% acetonitrile+0.05% of a 1% v/v solution of formic acid in water
Solvent B: 0.1% v/v solution of formic acid in 10 mM aqueous ammonium acetate
Gradient: Mixtures of Solvent A and Solvent B are used according to the following gradient profiles (expressed as % Solvent A in the mixture): 0% A/0.7 min, 0-100% A/3.5 min, 100% A/0.4 min, 100-0% A/0.2 min LCMS Method B LCMS instrumentation consists of the following:
Column: Acquity HPLC BEH $C_{18}$ 1.7 μm 2.1 mm×50 mm. Column oven set to 40 degrees centigrade
Solvent A: Water 0.1% Formic Acid+10 mM Ammonium Acetate
Solvent B: MeCN:Water 95:5+0.05% Formic Acid
Injection volume: 0.5p1
Injection technique: Partial loop overfill
UV detection: 220 to 330 nm
UV sampling rate: 40 points per second
MS scan range: 100 to 1000 amu
MS scanning rate: 0.2 second scan with a 0.1 second inter scan delay
MS scan function: Electrospray with pos neg switching
Cycle time: 2 minutes and 30 seconds
Gradient:

| Time | Flow ml/min | % A | % B |
| --- | --- | --- | --- |
| 0 | 1 | 97 | 3 |
| 0.1 | 1 | 97 | 3 |
| 1.4 | 1 | 0 | 100 |
| 1.9 | 1 | 0 | 100 |
| 2 | 1 | 97 | 3 |

LCMS Method C

The HPLC analysis was conducted on a Sunfire C18 column (30 mm×4.6 mm i.d. 3.5 μm packing diameter) at 30 degrees centigrade.
Solvent A=0.1% v/v solution of Formic Acid in Water.
Solvent B=0.1% v/v solution of Formic Acid in Acetonitrile.
The gradient employed was:

| Time (min) | Flow Rate (ml/min) | % A | % B |
| --- | --- | --- | --- |
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

Mass Directed Automated Preparative HPLC Methods

The methods for the mass-directed automated preparative HPLC used for the purification of compounds are described below:

Method A
Column
The column used is typically a Supelco LCABZ++ column whose dimensions are 20 mm internal diameter by 100 mm in length. The stationary phase particle size is 5 μm.
Solvents
A:. Aqueous solvent=Water+0.1% Formic Acid
B:. Organic solvent=MeCN:Water 95:5+0.05% Formic Acid
Make up solvent=MeOH:Water 80:20+50 mMol Ammonium Acetate
Needle rinse solvent=MeOH: Water:DMSO 80:10:10
Methods
There are five methods used depending on the analytical retention time of the compound of interest.
They all have a 15-minute runtime, which comprises of a 10-minute gradient followed by a 5-minute column flush and re-equilibration step.
compound retention time 1.5-2.2 mins=0-30% B
compound retention time 2.0-2.8 mins=5-30% B
compound retention time 2.5-3.0 mins=15-55% B
compound retention time 2.8-4.0 mins=30-80% B
compound retention time 3.8-5.5 mins=50-90% B
Flow Rate
All of the above methods have a flow rate of 20 ml/min
It is thought that basic compounds isolated by this method are formate salts.

Method B
Columns
Small Scale Prep Column
Supelcosil ABZ+Plus column whose dimensions are 21.2 mm internal diameter by 100 mm in length. The stationary phase particle size is 5 μm.
Large Scale Prep Column
Supelcosil ABZ+Plus column whose dimensions are 30.0 mm internal diameter by 150 mm in length. The stationary phase particle size is 12 μm.
Solvents
A: Aqueous solvent=Water+0.1% Formic Acid
B: Organic solvent=MeCN:Water 95:5+0.05% Formic Acid
Make up solvent to ZQ=MeOH:Water 80:20+50 mMol Ammonium Acetate
2767 Needle rinse solvent=MeOH: Water:DMSO 80:10:10
Methods for Small Scale Prep for up to 30 mg
There are ten methods available for use. The choice of method is dependant on the analytical retention time of the compound of interest (MDP=retention time as determined by LCMS Method A above).
Five methods have a 15-minute runtime, this comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.
compound retention time 1.5-2.2 mins=00-30% B
compound retention time 2.0-2.8 mins=10-40% B
compound retention time 2.5-3.0 mins=15-55% B
compound retention time 2.8-4.0 mins=30-80% B
compound retention time 3.8-5.5 mins=60-90% B
Flow rates for the above methods are 20 ml/min
Methods for Large Scale Prep for up to 90 mgs
Due to the different column dimension and the phase particle size the percentage organic content varies slightly to the small scale methods. As for small scale there are ten methods available for use. The choice of method is dependant on the analytical retention time of the compound of interest interest (MDP=retention time as determined by LCMS Method A above).

Five methods have a 15-minute runtime, which comprises of a 10-minute gradient followed by a 5-minute column flush and re-equilibration step. The other five have a 25-minute runtime. Here the methods have the same starting and end points for the organic content of B but the gradients have been extended over a 20-minute period to provide greater chromatographic resolution.
compound retention time 1.5-2.2 mins=00-30% B
compound retention time 2.0-2.8 mins=10-40% B
compound retention time 2.5-3.0 mins=25-55% B
compound retention time 2.8-4.0 mins=40-75% B
compound retention time 3.8-5.5 mins=60-90% B
Flow rates for the above methods are 40 ml/min It is thought that basic compounds isolated by this method are formate salts.

Mass Directed Automated Preparative HPLC Column, Conditions and Eluent
Method C
Column details: Zorbax Eclipse XDB-C18 prep HT (dimensions 212×100 mm, 5 um packing)
Software/hardware: Agilent 1100 series LC/MSD hardware, chemstation 32 purification software. Collects on uv/mass ion trigger
Solvents:
A=0.1% v/v solution of Trifluoroacetic Acid in Water.
B=0.1% v/v solution of Trifluoroacetic Acid in Acetonitrile.
20 ml/min solvent speed, gradient elution:
1 min 90% Water (0.1% TFA):10% MECN (0.1% TFA) increasing over 9 mins to 5% Water (0.1% TFA):95% MECN (0.1% TFA) to elute compounds.
Mass Directed Automated Preparative Hplc Column, Conditions and Eluent
Method D
Column Details: XBRIDGE C18 column (100 mm×19 mm id 5 uM packing diameter)
Solvents
A=10 mM ammonium bicarbonate in water adjusted to pH 10 with aq. ammonia solution
B=Acetonitrile
The UV detection was an averaged signal from wavelength of 210 nm to 350 nm and mass spectra were recorded on a mass spectrometer using an alternate-scan positive and negative mode electrospray ionization.
Mass Directed Automated Preparative HPLC Column, Conditions and Eluent
Method E
Mass Directed Auto Prep System consists of:
Waters ZQ Mass spectrometer
Waters 2525 pump
Waters Reagent Manager
Waters 2767 autosampler
Gilson 202 autosampler
Gilson 115 UV detector
Splitter box
Phenomenex column switcher
Injection volume: 0.5 ml
Flow rate (mobile phase): 20 ml/minute
Column: Supelco ABZ+ plus 100 mm×21.2 mm, 5 um
Mobile Phase: A) 0.1% v/v solution of formic acid in water.
B) 95% acetonitrile+5% of a 1% v/v solution of formic acid in water.
Make up Flow: 80% methanol+20% 0.1% v/v solution of formic acid in 10 mM aqueous ammonium acetate.

Two injections per sample were made on the generic methods 2.5-3.0 and 2.8-4.0.

| | Gradient | |
|---|---|---|
| Time (minutes) | 2.5-3.0 % B | 2.8-4.0 % B |
| 0 | 15 | 30 |
| 1 | 15 | 30 |
| 10 | 55 | 85 |
| 14 | 99 | 99 |
| 14.8 | 99 | 99 |
| 15 | 15 | 30 |

Intermediates and Examples

When the name of a commercial supplier is given after the name of a compound or a reagent, for instance "compound X (Aldrich)" or "compound X/Aldrich", this means that compound X is obtainable from a commercial supplier, such as the commercial supplier named. If not referenced herein the compound or reagent can be purchased from a standard supplier such as Sigma Aldrich, Lancaster, Fluorochem, TCI etc.

Similarly, when a literature or a patent reference is given after the name of a compound, for instance compound Y (EP 0 123 456), this means that the preparation of the compound is described in the named reference.

The names of the Examples have been obtained using a compound naming programme which matches name to structure (e.g. ACD/Name Batch v 9.0).

Intermediate 1

6-Bromo-4-nitro-2-(tetrahydro-2H-pyran-2-yl)-2H-indazole

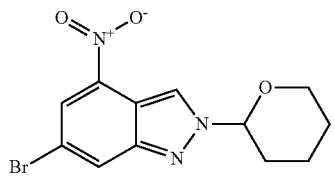 [SMILES: O=[N+]([O-])c1cc(Br)cc2nn(C3CCCCO3)cc12]

A mixture of 6-bromo-4-nitro-1H-indazole (10.0 g, 0.041 mol), 3,4-dihydropyran (8.52 ml, 0.09 mol) and pyridinium para-toluene sulfonate (125 mg, 0.50 mol) in dichloromethane (150 ml) was heated at reflux for 4.5 hours. The reaction was allowed to cool to room temperature and was poured onto saturated aqueous sodium bicarbonate (200 ml). The layers were separated and the aqueous layer extracted with dichloromethane (2×100 ml). The combined organic layers were washed with 5% aqueous citric acid (w/v, 100 ml) and brine (100 ml) then dried over magnesium sulphate. Solvent was removed in vacuo to give the title compound which was used in subsequent reactions without further purification (12.89 g).

LCMS (Method A) m/z 326 [MH$^+$]; R$_t$=3.42 min.

Intermediate 2

6-(1H-Indol-4-yl)-4-nitro-2-(tetrahydro-2H-pyran-2-yl)-2H-indazole

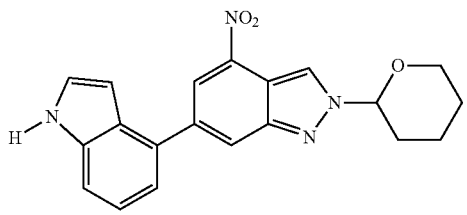 [SMILES: O=[N+]([O-])c1cc(-c2cccc3[nH]ccc23)cc2nn(C3CCCCO3)cc12]

Five reactions were set up with 6-bromo-4-nitro-2-(tetrahydro-2H-pyran-2-yl)-2H-indazole (500 mg, 1.53 mmol), [1,1'-bis(diphenylphosphino)ferrocene]dichloropalladium (II) (125 mg, 0.153 mmol), 1H-indol-4-ylboronic acid (370 mg, 2.3 mmol), saturated aqueous sodium hydrogen carbonate (3 ml) and isopropyl alcohol (12 ml) in each. They were all heated at 150° C. for 10 minutes in the microwave. The reaction mixtures were combined and water (250 ml) and ethyl acetate (250 ml) added. The mixture was filtered and the organic layer collected. The organic layer was washed with water followed by brine. The organic layer was dried over magnesium sulphate, filtered and solvent removed in vacuo. The residue was dissolved in dichloromethane and pre-absorbed onto silica. Purification was carried out using chromatography on silica eluting with 0-25% ethyl acetate in cyclohexane. The desired fractions were collected and combined and solvent removed in vacuo to give the title compound as a yellow solid (1.72 g).

LCMS (Method A) m/z 363 [MH$^+$], R$_t$=3.61 min.

Intermediate 3

6-(1H-Indol-4-yl)-2-(tetrahydro-2H-pyran-2-yl)-2H-indazol-4-amine

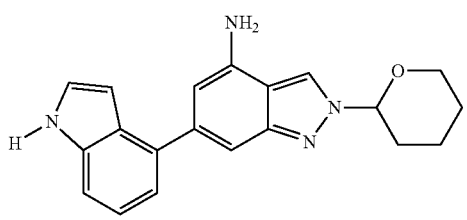 [SMILES: Nc1cc(-c2cccc3[nH]ccc23)cc2nn(C3CCCCO3)cc12]

6-(1H-Indol-4-yl)-4-nitro-2-(tetrahydro-2H-pyran-2-yl)-2H-indazole (714 mg, 1.97 mmol) was dissolved in ethylacetate (100 ml) and the compound was hydrogenated using the H-cube™ (available from THALESNano) using 10% Pd/C catalyst at 30° C. and under 30 bar pressure of hydrogen. Solvent was removed in vacuo. The title compound was isolated as an orange/brown solid (629 mg) which was used in subsequent reactions without further purification.

LCMS (Method A) m/z 333 [MH$^+$], R$_t$=2.86 min.

Intermediate 4

6-(1H-Indol-4-yl)-1H-indazol-4-amine

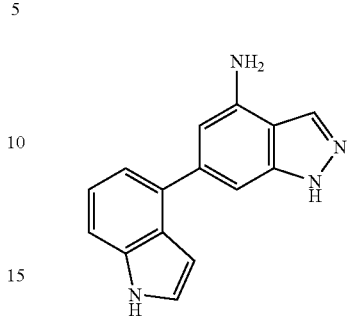

6-Bromo-1H-indazol-4-amine (10 g, available from Sinova Inc.) and 4-(4,4,5,5-tetramethyl-1,3,2-dioxaborolan-2-yl)-1H-indole (16.05 g, available from Frontier Scientific, Europe Ltd) were dissolved in 1,4-dioxane (60 ml) and water (60 ml). 2M sodium carbonate (70.7 ml) and Pd(dppf)Cl$_2$-DCM adduct (1.93 g) were added and the mixture was heated at 115° C. for 18 hr. The reaction mixture was diluted with dichloromethane (200 ml) and the organic and aqueous layers were separated by hydrophobic frit. The aqueous layer was extracted with further quantities of dichloromethane (2×200 ml), using a hydrophobic frit to separate the layers. The organic layers were combined and silica (80 g) was added. The solvent was removed in vacuo to give a crude material that was purified by chromatography on silica gel (750 g cartridge, Flashmaster II) eluting with 0-100% ethyl acetate in cyclohexane over 60 minutes. The oil was dried in vacuo on a drying rack overnight. The resultant yellow foam was dissolved in dichloromethane (3×400 ml), removing the solvent in vacuo after each dissolution. Ethyl acetate (50 ml) was then added and the solvent was removed in vacuo. The solid obtained was dried in a vacuum oven to afford the title compound (12.8 g) as a yellow foam.

LCMS (Method A) m/z 249 [MH$^+$], R$_t$ 2.71 mins.

Intermediate 5

4-(1,1-Dimethylethyl) 2-(phenylmethyl) 2,4-morpholinedicarboxylate

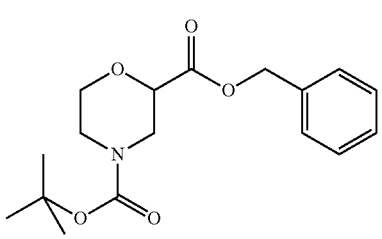 [SMILES: CC(C)(C)OC(=O)N1CCOC(C(=O)OCc2ccccc2)C1]

4-{[(1,1-Dimethylethyl)oxy]carbonyl}-2-morpholinecarboxylic acid [Supplied by NeoMPS] (1 g, 4.32 mmol) was dissolved in N,N-dimethylformamide (20 ml) and potassium carbonate (0.598 g, 4.32 mmol) added. The mixture was stirred under nitrogen for 15 minutes at 20° C. Bromomethylbenzene (0.514 ml, 4.32 mmol) was added and the mixture stirred under nitrogen at room temperature for 18 hr. Water (25 ml) and dichloromethane (20 ml) were added and separated by hydrophobic fit. The aqueous phase was extracted with dichloromethane (2×20 ml). The organic phases were combined and the solvent was removed in vacuo. To the residue 1% lithium chloride solution (20 ml) and diethyl ether (20 ml) were added. The phases were separated and the aqueous phase was extracted with diethyl ether (2×15 ml). The combined organic phases were dried over magnesium sulphate and the solvent was removed in vacuo to give the title compound (1.19 g) as a colourless oil.

LCMS (Method A): m/z 322 [MH$^+$], R$_t$=3.28 min.

Intermediate 6

Phenylmethyl 2-morpholinecarboxylate

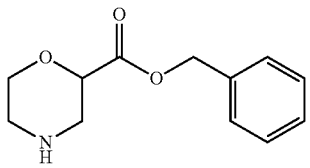 [SMILES: O=C(OCc1ccccc1)C1CNCCO1]

4-(1,1-Dimethylethyl) 2-(phenylmethyl) 2,4-morpholinedicarboxylate (1.19 g, 3.70 mmol) was dissolved in 1,4-dioxane (2 ml). Hydrogen chloride (4M) in 1,4-dioxane (20 ml, 80 mmol) was added and the mixture was stirred at room temperature under nitrogen for 4 hr. The solvent was removed in vacuo to give a white solid. The solid was dried in a vacuum oven overnight to give the title compound (908 mg) as a white solid.

LCMS (Method A): m/z 222 [MH$^+$], R$_t$=1.93 min

Intermediate 7

Phenylmethyl 4-acetyl-2-morpholinecarboxylate

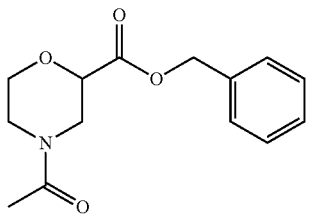 [SMILES: CC(=O)N1CCOC(C(=O)OCc2ccccc2)C1]

Phenylmethyl 2-morpholinecarboxylate (450 mg, 2.034 mmol) was dissolved in dichloromethane (30 ml). DIPEA (0.71 ml, 4.07 mmol) and acetic anhydride (0.23 ml, 2.441 mmol) were added and the mixture was stirred under nitrogen at room temperature for 18 hr. The solvent was removed in vacuo, the residue was portioned between dichloromethane (20 ml) and water (20 ml) and separated by hydrophobic frit. The aqueous layer was washed with dichloromethane (2×10 ml) and to the combined organic phases was added saturated sodium bicarbonate solution (20 ml). The phases were separated by hydrophobic frit and the aqueous layer was washed with dichloromethane (2×10 ml). The solvent was removed in vacuo, the residue was dissolved in dichloromethane (~5 ml) and the residue was purified by flash chromatography (20 g silica, gradient elution, 0-100% EtOAc-Cyclohexane then 0-20% MeOH). The solvent was removed in vacuo to give the title compound (313 mg, 1.19 mmol) as a colourless oil.

LCMS (Method A): m/z 264 [MH$^+$], R$_t$=2.47 min.

Intermediate 8

4-Acetyl-2-morpholinecarboxylic acid

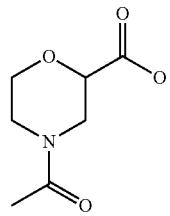

Phenylmethyl 4-acetyl-2-morpholinecarboxylate (313 mg, 1.189 mmol) was dissolved in ethanol (5 ml) and hydrogenated at 30 bar on H-Cube using 10% palladium on carbon. The mixture was blown to dryness under a stream of nitrogen to give the starting material. The starting material was dissolved in ethanol (5 ml) and hydrogenated at 50 bar on H-Cube using10% palladium on carbon. The mixture was blown to dryness under a stream of nitrogen to give the title compound (50 mg) as a colourless oil.

LCMS (Method A): m/z 174 [MH$^+$], R$_t$=0.48 min

Example 1

N-[6-(1H-Indol-4-yl)-1H-indazol-4-yl]benzamide

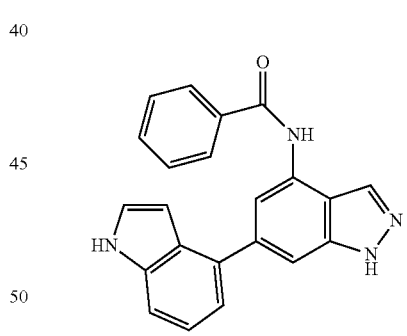

Benzoic acid (10 mg, 0.08 mmol) in DMF (0.2 mL) was treated with HATU (27 mg, 0.07 mmol) in DMF (0.2 mL) and DIPEA (30 µL, 0.24 mmol). The reaction mixture was shaken for five minutes prior to treatment with 6-(1H-indol-4-yl)-2-(tetrahydro-2H-pyran-2-yl)-2H-indazol-4-amine (20 mg, 0.06 mmol) in DMF (0.2 mL). Reaction mixture was shaken for five minutes and left to stand at 22° C. for 18 hrs. Solvent was removed in vacuo and the product re-dissolved in methanol (1 mL) prior to application on to an SCX cartridge (1 g). Product was eluted after 1 hr with 2M ammonia in methanol (2×3 mL), fractions were combined and concentrated under a stream of nitrogen using blow down apparatus. Purification by MDAP (Method D) afforded the title compound.

LCMS (Method A) m/z 353 [MH$^+$], R$_t$=3.18 min.

Similarly prepared were:

| Example number | Name | Structure | Precursor Acid | LCMS $R_t$ | MH$^+$ |
|---|---|---|---|---|---|
| 2 | 2-fluoro-N-[6-(1H-indol-4-yl)-1H-indazol-4-yl]benzamide | 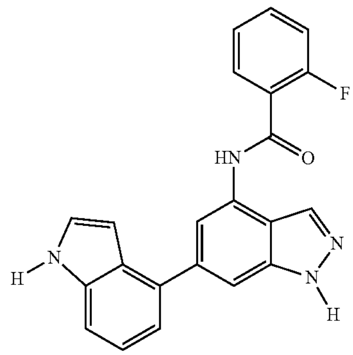 [SMILES: O=C(Nc1cc(-c2cccc3[nH]ccc23)cc2[nH]ncc12)c1ccccc1F] | 2-fluorobenzoic acid | 3.23 | 371 |
| 3 | 2,3-difluoro-N-[6-(1H-indol-4-yl)-1H-indazol-4-yl]benzamide | 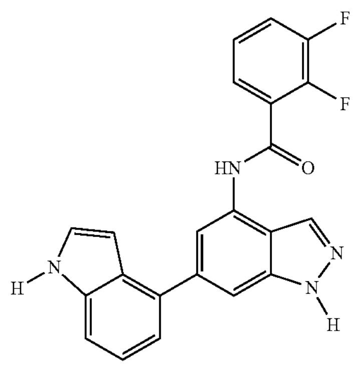 [SMILES: O=C(Nc1cc(-c2cccc3[nH]ccc23)cc2[nH]ncc12)c1cccc(F)c1F] | 2,3-difluorobenzoic acid | 3.28 | 389 |
| 4 | 2,5-difluoro-N-[6-(1H-indol-4-yl)-1H-indazol-4-yl]benzamide | 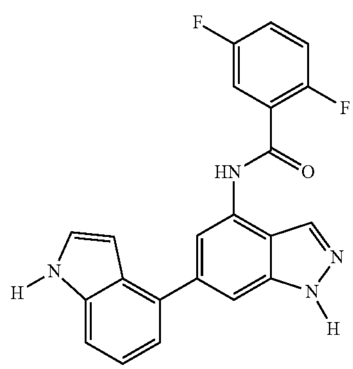 [SMILES: O=C(Nc1cc(-c2cccc3[nH]ccc23)cc2[nH]ncc12)c1cc(F)ccc1F] | 2,5-difluorobenzoic acid | 3.31 | 389 |
| 5 | N-[6-(1H-indol-4-yl)-1H-indazol-4-yl]-2-methyl-benzamide | 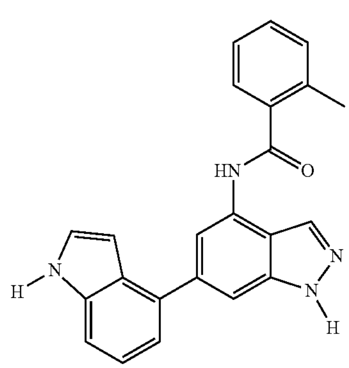 [SMILES: Cc1ccccc1C(=O)Nc1cc(-c2cccc3[nH]ccc23)cc2[nH]ncc12] | 2 methylbenzoic acid | 3.23 | 367 |

| Example number | Name | Structure | Precursor Acid | LCMS R$_t$ | MH$^+$ |
|---|---|---|---|---|---|
| 6 | 2'-chloro-N-[6-(1H-indol-4-yl)-1H-indazol-4-yl]-2-biphenyl-carboxamide | 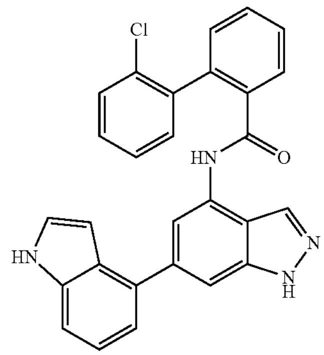 [SMILES: O=C(Nc1cc(-c2cccc3[nH]ccc23)cc2[nH]ncc12)c1ccccc1-c1ccccc1Cl] | 2-[(1Z)-2-chloro-1-ethenyl-1,3-butadien-1-yl]benzoic acid (available from Apollo Scientific) | 3.45 | 463 |
| 7 | N-[6-(1H-indol-4-yl)-1H-indazol-4-yl]-1-isoquinoline-carboxamide | 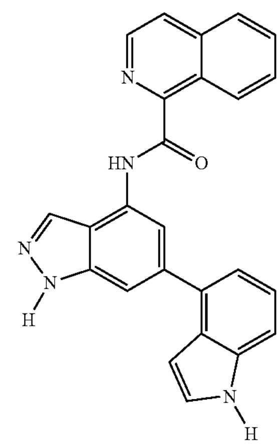 [SMILES: O=C(Nc1cc(-c2cccc3[nH]ccc23)cc2[nH]ncc12)c1nccc2ccccc12] | 1-isoquinoline-carboxylic acid | 3.68 | 404 |

Example 8

2,4-Difluoro-N-[6-(1H-indol-4-yl)-1H-indazol-4-yl]benzamide

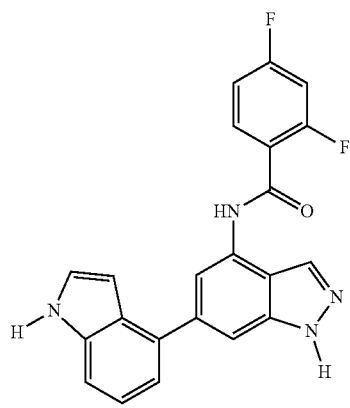 [SMILES: O=C(Nc1cc(-c2cccc3[nH]ccc23)cc2[nH]ncc12)c1ccc(F)cc1F]

2-4-Difluorobenzoic acid (9 mg, 0.06 mmol) in DMF (0.2 mL) was treated with HATU (27 mg, 0.07 mmol) in DMF (0.2 mL) and di-isopropylethylamine (0.030 mL, 0.24 mmol). Reaction mixture was shaken for five minutes prior to treatment with 6-(1H-indol-4-yl)-2-(tetrahydro-2H-pyran-2-yl)-2H-indazol-4-amine (20 mg, 0.06 mmol) in DMF (0.2 mL). Reaction mixture was shaken for five minutes and left to stand at 22° C. for 18 hrs. Solvent was removed in vacuo and the product re-dissolved in methanol (0.5 mL) prior to application on to an SCX cartridge (1 g). Product was eluted after 1 hr with 2M ammonia in methanol (2×3 mL), fractions were combined and concentrated under a stream of nitrogen using blow down apparatus. Purification by MDAP (Method D) afforded the title compound.

LCMS (Method A) m/z 389 [MH$^+$], R$_t$=1.04 min.

Similarly prepared were:

| Example number | Name | Structure | Precursor acid | LCMS Rt (min) | MH+ |
|---|---|---|---|---|---|
| 9 | 2,6-difluoro-N-[6-(1H-indol-4-yl)-1H-indazol-4-yl]benzamide | 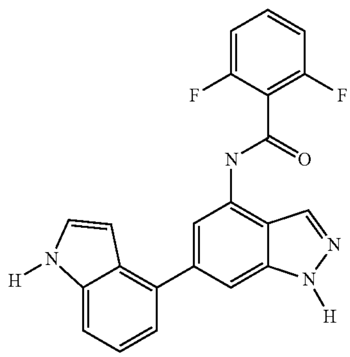 [SMILES: O=C(Nc1cc(-c2cccc3[nH]ccc23)cc2[nH]ncc12)c1c(F)cccc1F] | 2,6-difluorobenzoic acid | 0.99 | 389 |
| 10 | N-[6-(1H-indol-4-yl)-1H-indazol-4-yl]-2-(methyloxy)benzamide | 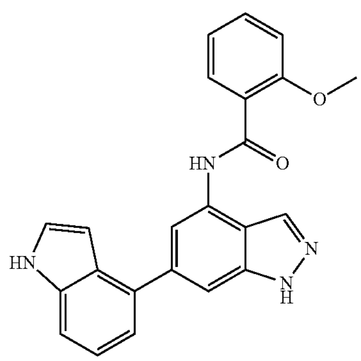 [SMILES: COc1ccccc1C(=O)Nc1cc(-c2cccc3[nH]ccc23)cc2[nH]ncc12] | 2-(methloxy) benzoic acid | 1.06 | 383 |
| 11 | 2-[(difluoromethyl)oxy]-N-[6-(1H-indol-4-yl)-1H-indazol-4-yl]benzamide | 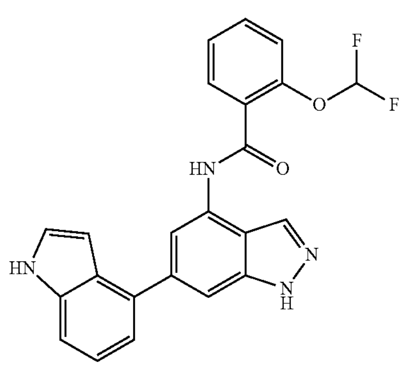 [SMILES: O=C(Nc1cc(-c2cccc3[nH]ccc23)cc2[nH]ncc12)c1ccccc1OC(F)F] | 2-[(difluoromethyl)oxy]benzoic acid (available from JRD Fluorochemicals Ltd) | 1.04 | 419 |

Example 12

N-[6-(1H-Indol-4-yl)-1H-indazol-4-yl]pyrazolo[1,5-a]pyridine-2-carboxamide

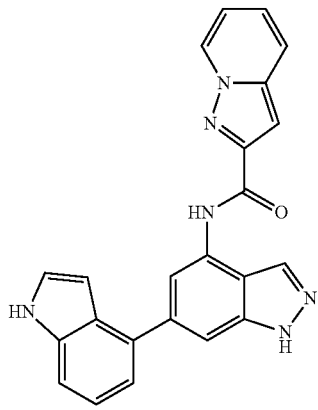 [SMILES: O=C(Nc1cc(-c2cccc3[nH]ccc23)cc2[nH]ncc12)c1cc2ccccn2n1]

Pyrazolo[1,5-a]pyridine-2-carboxylic acid (27 mg, 0.166 mmol) was treated with anhydrous THF (2 ml) and then 1-chloro-N,N,2-trimethylpropenylamine (0.026 ml, 0.20 mmol). The reaction was stirred at room temperature under nitrogen for 2 hrs. The reaction was then treated with anhydrous DIPEA (0.131 ml, 0.753 mmol) and 2 ml of solution of 6-(1H-indol-4-yl)-2-(tetrahydro-2H-pyran-2-yl)-2H-indazol-4-amine (750 mg, 2.26 mmol) in THF (30 ml). The reaction was then stirred at room temperature under nitrogen for 69 hrs. The solvent was blown-off under a stream of nitrogen, dissolved in methanol (3 ml) and then solvent removed under reduced pressure. The crude reaction mixture was dissolved in methanol (5 ml), treated with Macroporous Tosic Acid (4.45 mmol/g, 102 mg, 0.45 mmol), stirred at room temperature for 17 hrs and then treated with 0.88 ammonia (0.5 ml), stirred for 30 minutes and then filtered. The solvent was removed under reduced pressure and then the residue purified by Mass Directed Automated Preparative HPLC (Method B) to give the title compound.

LCMS (Method B) m/z 393 [MH$^+$], R$_t$=1.02 min.

Similarly prepared was:

Example 14

N-[6-(1H-Indol-4-yl)-1H-indazol-4-yl]-1H-benzimidazole-2-carboxamide

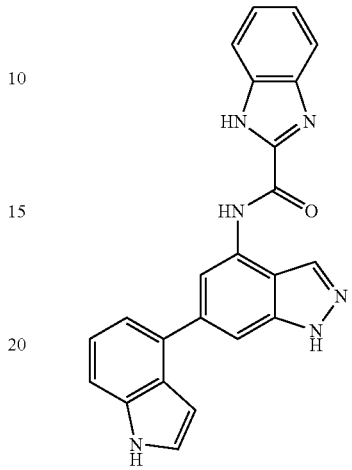

1H-Benzimidazole-2-carboxylic acid (available from Apollo Scientific, 25 mg, 0.151 mmol), O-(7-Azabenzatriazol-1-yl)-N,N,N',N'-tetramethyluronium hexafluorophosphate (63 mg, 0.17 mmol) and 6-(1H-indol-4-yl)-2-(tetrahydro-2H-pyran-2-yl)-2H-indazol-4-amine (50 mg, 0.15 mmol) were dissolved in anhydrous DMF (3 ml) and then treated with DIPEA (0.05 ml, 0.30 mmol). The reactions were then stirred at room temperature for 15 hours. The mixture was treated with methanol (3 ml) and then Macroporous-Tosic Acid (170 mg, 0.75 mmol) then stirred for 15 hours. The mixture was then treated with 0.88 ammonia solution (0.60 ml), stirred for 10 minutes, then filtered and solvent blown off under a stream of nitrogen. The crude residue was purified by Mass Directed Automated Preparative HPLC (Method B) to give after evaporation of solvents the title compound as a yellow solid (27 mg). LCMS (Method B) m/z 393 [MH$^+$], R$_t$=1.04 min.

The compound listed in the table below was synthesised using the method above.

| Example number | Name | Structure | Acid Monomer | Rt min | MH$^+$ |
|---|---|---|---|---|---|
| 13 | N-[6-(1H-indol-4-yl)-1H-indazol-4-yl]-6-(methyloxy)-2-pyrazine-carboxamide | 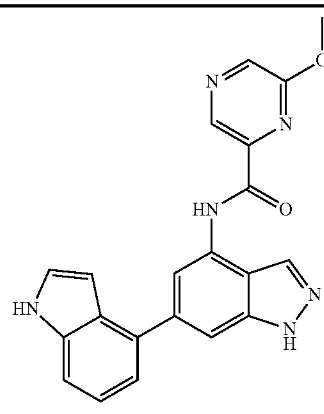 | | 1.01 | 385 |

| Example number | Name | Structure | Acid Monomer | Rt Min | MH+ |
|---|---|---|---|---|---|
| 15 | N-[6-(1H-indol-4-yl)-1H-indazol-4-yl]-1H-indole-2-carboxamide | 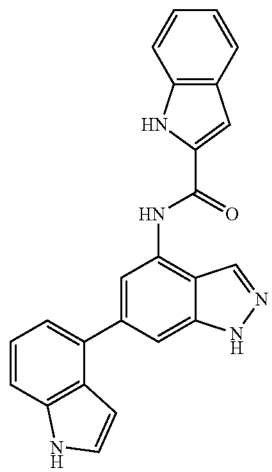 [SMILES: O=C(Nc1cc(-c2cccc3[nH]ccc23)cc2[nH]ncc12)c1cc2ccccc2[nH]1] | | 1.09 | 392 |

Example 16

N-[6-(1H-Indol-4-yl)-1H-indazol-4-yl]-4-methyl-2-(methyloxy)benzamide

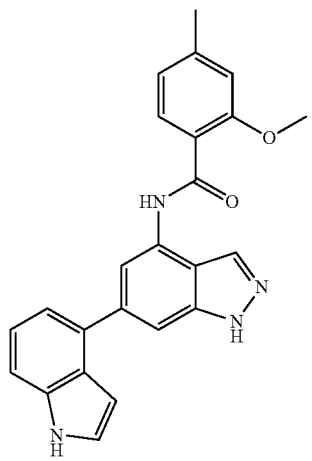 [SMILES: COc1cc(C)ccc1C(=O)Nc1cc(-c2cccc3[nH]ccc23)cc2[nH]ncc12]

To a solution of 4-methyl-2-(methyloxy)benzoic acid (67 mg, 0.40 mmol) in DMF (1 ml) were added HATU (248 mg, 0.40 mmol) and DIPEA (0.211 mL, 1.21 mmol). The mixture was stirred for 30 mins under nitrogen before addition of 6-(1H-indol-4-yl)-1H-indazol-4-amine (50 mg, 0.201 mmol). The reaction was stirred for 2 h then it was loaded onto PS-aminopropyl cartridge (5 g) and left for 3 h. The cartridge was washed with 10% MeOH in DCM. Appropriate fractions were combined and the solvent was evaporated. The residue was dissolved in MeOH: DMSO (1 ml; 1:1, v/v) and purified by Mass Directed Automated Preparative HPLC using method B. Solvent was evaporated under a stream of nitrogen to give title compound (13 mg).

LCMS (Method B) m/z 397 [MH+], $R_t$=1.12 mins.

Example 17

N-[6-(1H-Indol-4-yl)-1H-indazol-4-yl]-5-methyl-2-(methyloxy)benzamide

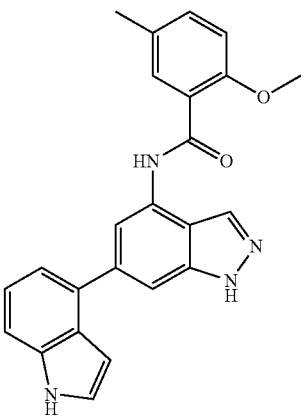 [SMILES: COc1ccc(C)cc1C(=O)Nc1cc(-c2cccc3[nH]ccc23)cc2[nH]ncc12]

To a solution of 5-methyl-2-(methyloxy)benzoic acid (67 mg, 0.40 mmol) in DMF (1 ml), HATU (248 mg, 0.40 mmol) and DIPEA (156 mg, 1.208 mmol) were added. The reaction was stirred for 30 mins under nitrogen before addition of 6-(1H-indol-4-yl)-1H-indazol-4-amine (50 mg, 0.20 mmol). The reaction was stirred for 3 h then it was loaded onto a PS-aminopropyl cartridge and left for 3 h. The cartridge was washed with 10% MeOH in DCM. Appropriate fractions were combined and the solvent was evaporated. The residue was dissolved in MeOH:DMSO (1 ml; 1:1, v/v) and purified by Mass Directed Automated Preparative HPLC using method B. The solvent was dried under a stream of nitrogen. The residue was dissolved in DMSO and further purified by HPLC using the following conditions:

Column: Supelco ABZ+ Plus, 5 μm, 100×21.2 mm i.d.
Solvent A: 0.1% Formic acid in water
Solvent B: 1% Formic acid in water:MeCN (5:95, v/v)
Flow rate: 20 ml/min
Gradient: 35-80% B over 25 minutes Appropriate fractions were evaporated under a stream of nitrogen to give the title compound (9 mg).

LCMS (Method B) m/z 397 [MH+], $R_t$=1.13 mins.

Example 18

N-[6-(1H-Indol-4-yl)-1H-indazol-4-yl]-2-(3-methyl-1H-pyrazol-1-yl)acetamide

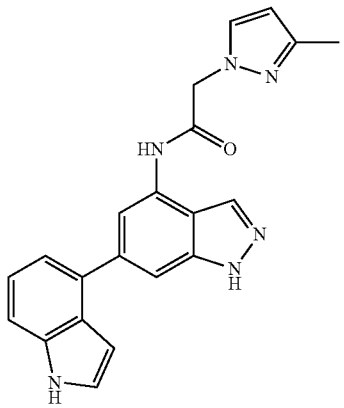 [SMILES: Cc1ccn(CC(=O)Nc2cc(-c3cccc4[nH]ccc34)cc3[nH]ncc23)n1]

(3-Methyl-1H-pyrazol-1-yl)acetic acid (38 mg, 0.27 mmol) (from Art-Chem GmbH), HATU (126 mg, 0.33 mmol) and DIPEA (0.158 ml, 0.91 mmol) were dissolved in DMF (2 ml) and stirred under nitrogen for 30 mins. 6-(1H-Indol-4-yl)-1-(tetrahydro-2H-pyran-2-yl)-1H-indazol-4-amine (100 mg, 0.30 mmol) was added and the reaction was stirred for 5 h. Further (3-methyl-1H-pyrazol-1-yl)acetic acid (38 mg, 0.27 mmol), HATU (126 mg, 0.33 mmol) and DIPEA (0.158 ml, 0.91 mmol) in DMF (1 ml) was added, after stirring together for 10 mins, and the reaction was stirred for 2 days under a nitrogen atmosphere at RT. The reaction was loaded on to a PS-aminopropyl cartridge (10 g) and eluted with DCM. Appropriate fractions were combined and evaporated in vacuo. MeOH (2 ml) and 2 M HCl (aq) (45 µl, 0.09 mmol) were added and stirred for ~30 mins at RT. The solvent was evaporated in vacuo and the residue was dissolved in MeOH:DMSO (2 ml; 1:1, v/v) and purified by Mass Directed Automated Preparative HPLC using method B. The solvent was dried under a stream of nitrogen to give title compound (31 mg).

LCMS (Method B) m/z 371 [MH$^+$], R$_t$=0.9 mins.

Example 19

N-[6-(1H-Indol-4-yl)-1H-indazol-4-yl]-3-methyl-2-(methyloxy)benzamide

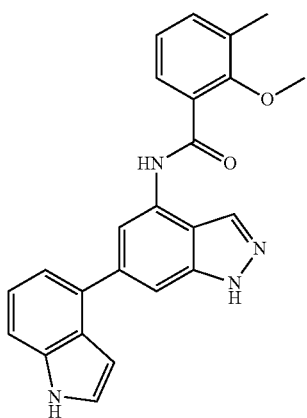 [SMILES: COc1c(C)cccc1C(=O)Nc1cc(-c2cccc3[nH]ccc23)cc2[nH]ncc12]

DMF (1 ml) was added to 3-methyl-2-(methyloxy)benzoic acid (134 mg, 0.81 mmol) (Apin Chemicals), HATU (306 mg, 0.81 mmol) and DIPEA (0.422 ml, 2.417 mmol). The reaction was stirred for 30 mins under nitrogen before addition of 6-(1H-indol-4-yl)-1H-indazol-4-amine (100 mg, 0.403 mmol). The reaction was stirred under nitrogen at RT overnight, then it was loaded onto a PS-aminopropyl cartridge and left for 3 h. The cartridge was washed with 10% MeOH in DCM. Appropriate fractions were combined and the solvent was evaporated. The residue was dissolved in MeOH:DMSO (2 ml; 1:1, v/v) and purified by Mass Directed Automated Preparative HPLC using method B. The solvent was dried under a stream of nitrogen to give title compound (6 mg).

LCMS (Method B) m/z 397 [MH$^+$], R$_t$=1.13 mins.

Example 20

2-(Ethyloxy)-N-[6-(1H-indol-4-yl)-1H-indazol-4-yl]benzamide

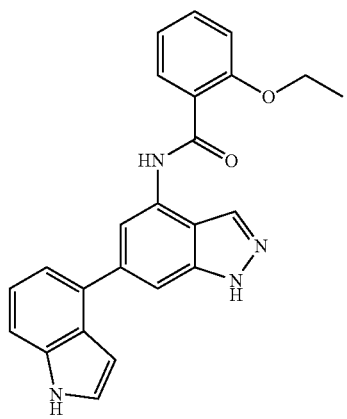 [SMILES: CCOc1ccccc1C(=O)Nc1cc(-c2cccc3[nH]ccc23)cc2[nH]ncc12]

To a solution of 2-(ethyloxy)benzoic acid (67 mg, 0.40 mmol) in DMF (1 ml), HATU (248 mg, 0.40 mmol) and DIPEA (0.211 mL, 1.21 mmol) were added. The reaction was stirred for 30 mins under nitrogen before addition of 6-(1H-indol-4-yl)-1H-indazol-4-amine (50 mg, 0.20 mmol). The reaction was stirred overnight then it was loaded onto a PS-aminopropyl cartridge (5 g) and left for 3 h. The cartridge was washed with 10% MeOH in DCM. Appropriate fractions were combined and the solvent was evaporated. The residue was dissolved in MeOH:DMSO (1 ml; 1:1, v/v) and purified by Mass Directed Automated Preparative HPLC using method B. Appropriate fractions were dried under a stream of nitrogen to give title compound, 27 mg.

LCMS (Method B) m/z 397 [MH$^+$], R$_t$=1.11 min.

Example 21

4-Acetyl-N-[6-(1H-indol-4-yl)-1H-indazol-4-yl]-2-morpholinecarboxamide

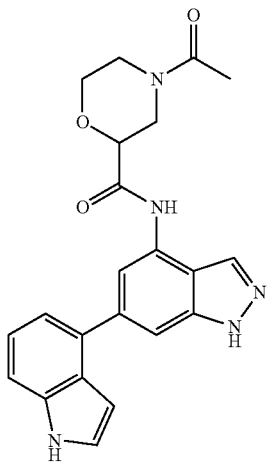 [SMILES: CC(=O)N1CCOC(C(=O)Nc2cc(-c3cccc4[nH]ccc34)cc3[nH]ncc23)C1]

To a solution of HATU (0.107 g, 0.28 mmol) in dry DMF (3 ml) was added 4-acetyl-2-morpholinecarboxylic acid (0.05 g, 0.282 mmol). DIPEA (0.098 ml, 0.56 mmol) was added and the mixture was left to stand for 10 min. 6-(1H-indol-4-yl)-1H-indazol-4-amine (0.04 g, 0.14 mmol), dissolved in dry DMF (3 ml) was added and the solution was left to stand at room temperature for 20 hr. DMF was removed by blow down under a stream of nitrogen, then the residue was dissolved and purified by Mass Directed AutoPrep Method B. The solvent was removed in vacuo and product dried in a vacuum oven at 50° C. overnight to give the title compound as a brown oil (17 mg).

LCMS (Method A): m/z 404 [MH$^+$], R$_t$=2.72 min.

Example 22

N-[6-(1H-Indol-4-yl)-1H-indazol-4-yl]-2-(2-pyridinyl)acetamide

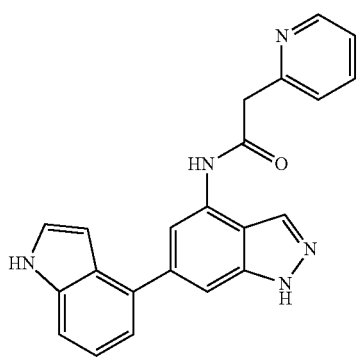 [SMILES: O=C(Cc1ccccn1)Nc1cc(-c2cccc3[nH]ccc23)cc2[nH]ncc12]

2-Pyridylacetic acid hydrochloride (0.033 g, 0.191 mmol), HATU (0.084 g, 0.220 mmol) and DIPEA (0.130 ml, 0.764 mmol) were combined in DMF (3 ml) and stirred at 20° C. for 10 minutes. 6-(1H-indol-4-yl)-2-(tetrahydro-2H-pyran-2-yl)-2H-indazol-4-amine (0.07 g, 0.20 mmol) was added and the reaction was stirred for 5 h at 20° C. A second batch of 2-pyridylacetic acid hydrochloride (0.033 g, 0.191 mmol), HATU (0.084 g, 0.220 mmol) and DI PEA (0.130 ml, 0.764 mmol) in DMF (3 ml) was prepared and stirred at 20° C. for 10 minutes. It was added to the main reaction mixture and stirred for 3 days (weekend) at 20° C. The reaction mixture was applied to a 5 g NH2-SPE cartridge and eluted with 10% methanol in dichloromethane. The solvent was evaporated and the residue was purified by Mass Directed Auto Prep (Method B) to give the title compound (0.018 g).

LCMS (Method B) shows m/z 368 [MH$^+$], R$_t$=0.83 min.

Example 23

2-[6-(1H-Indol-4-yl)-1H-indazol-4-yl]-1H-isoindole-1,3(2H)-dione

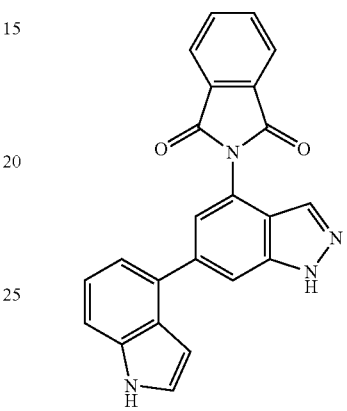

A mixture of 6-(1H-indol-4-yl)-1H-indazol-4-amine (500 mg, 2.014 mmol), 2-benzofuran-1,3-dione (298 mg, 2.014 mmol) and DMF (2.5 ml) was placed in a Biotage vial (2-5 ml) equipped with a magnetic stirrer bar. The vial was placed in a Biotage Initiator microwave and heated at 150° C. for 30 min then again at 150° C. for a further 15 min. The reaction mixture was evaporated to dryness to give a brown oil which was dissolved in dichloromethane and applied to a 100 g silica SPE cartridge. The cartridge was eluted on a Flashmaster (II) instrument using a gradient of 0-100% ethyl acetate in cyclohexane over 40 min followed by 0-20% methanol in cyclohexane over 15 min. Appropriate fractions were combined and evaporated to give the title compound (481 mg) as a pale yellow foam.

LCMS (Method B) shows m/z 379 [MH$^+$], R$_t$=1.04 min.

Example 24

2-[6-(1H-Indol-4-yl)-1H-indazol-4-yl]-2,3-dihydro-1H-isoindol-1-one

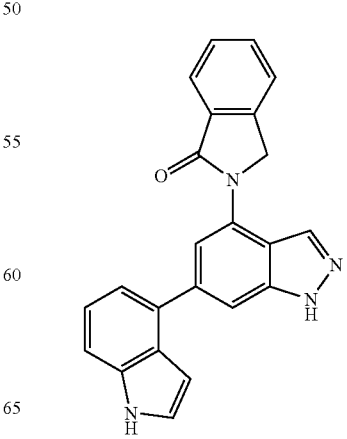

A mixture of 6-(1H-indol-4-yl)-1H-indazol-4-amine (100 mg, 0.403 mmol) and 1,2-benzenedicarbaldehyde (54 mg, 0.403 mmol) in ethyl acetate (1 ml) and acetic acid (0.25 ml) was stirred under a nitrogen atmosphere at room temperature for 3 h then overnight at room temperature. The reaction mixture was diluted with ethyl acetate (20 ml) and washed with 5% sodium bicarbonate solution (10 ml). The phases were separated, and the aqueous phase was extracted with further ethyl acetate (20 ml). The combined organic extracts (which contained a small amount of insoluble solid) were dried over anhydrous sodium sulphate, filtered and evaporated to give a yellow foam. This was partially dissolved in ethyl acetate (20 ml) and pre-adsorbed on silica (1.5 g). This silica was then added to the top of a 20 g silica SPE cartridge. The cartridge was eluted on a Flashmaster (II) instrument using a gradient of 0-100% ethyl acetate in cyclohexane over 30 min. Appropriate fractions were combined and evaporated to give the title compound (20 mg) as a pale yellow solid.

LCMS (Method B) shows m/z 365 [MH$^+$], R$_t$=1.00 min.

Example 25

N-[6-(1H-Indol-4-yl)-1H-indazol-4-yl]-3-methylbenzamide

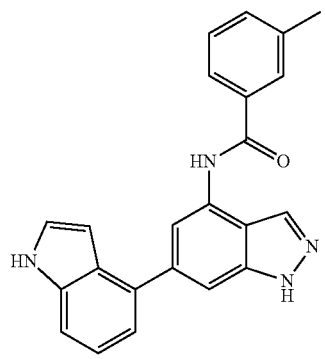 [SMILES: Cc1cccc(C(=O)Nc2cc(-c3cccc4[nH]ccc34)cc3[nH]ncc23)c1]

3-Methylbenzoic acid (60 mg, 0.44 mmol) was treated with HATU (168 mg, 0.44 mmol) in DMF (0.750 mL) and DIPEA (0.15 mL, 0.86 mmol). The mixture was shaken for five minutes prior to treatment with 6-(1H-indol-4-yl)-1H-indazol-4-amine (50 mg, 0.2 mmol) in DMF (0.350 mL) and was then left to stand at room temperature for 16 hrs. Solvent was removed in vacuo and the product re-dissolved in chloroform (0.3 mL) prior to application on to a pre-conditioned (methanol then chloroform) NH2 cartridge (1 g). Product was eluted after 2 hr with ethyl acetate/methanol (1:1, 3.2 mL), and concentrated under a stream of nitrogen using blow down apparatus. Purification by MDAP (Method C) afforded the title compound.

LCMS (Method A) m/z 367 [MH$^+$], R$_t$=3.30 min.

Example 26

N-[6-(1H-Indol-4-yl)-1H-indazol-4-yl]-4-methyl-2-morpholinecarboxamide

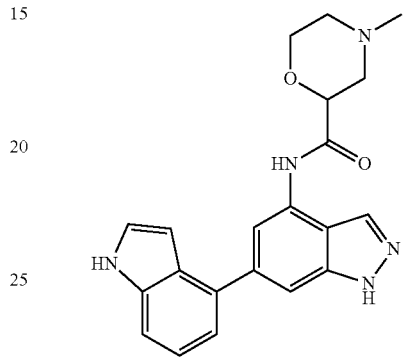

4-Methyl-2-morpholinecarboxylic acid hydrochloride (40 mg, 0.22 mmol) was treated with HATU (84 mg, 0.22 mmol) in DMF (0.250 mL) and DIPEA (0.069 mL, 0.40 mmol). The mixture was shaken for five minutes prior to treatment with 6-(1H-indol-4-yl)-1H-indazol-4-amine (25 mg, 0.1 mmol) in DMF (0.25 mL). Reaction mixture was left to stand at room temperature for 18 hrs. Solvent was removed in vacuo and the product re-dissolved in chloroform (0.3 mL) prior to application on to a pre-conditioned (methanol then chloroform) NH2 cartridge (0.5 g). Product was eluted after 2 hr with ethyl acetate/methanol (1:1, 3 mL), and concentrated under a stream of nitrogen using blow down apparatus. Purification by MDAP (Method D) afforded the title compound.

LCMS (Method B) m/z 376 [MH$^+$], R$_t$=0.60 min

Similarly prepared was:

| Example Number | Name | Structure | Precursor acid | LCMS Rt (min) | MH$^+$ |
|---|---|---|---|---|---|
| 27 | 1-acetyl-N-[6-(1H-indol-4-yl)-1H-indazol-4-yl]-4-piperidine-carboxamide | 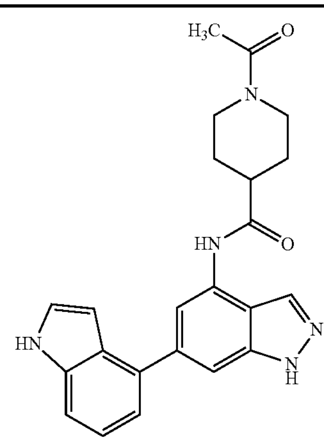 | 1-acetyl-4-piperidine-carboxylic acid | 0.8 | 402 |

-continued

| Example Number | Name | Structure | Precursor acid | LCMS Rt (min) | MH+ |
|---|---|---|---|---|---|
| 28 | N-[6-(1H-indol-4-yl)-1H-indazol-4-yl]-1-methyl-4-piperidine-carboxamide | 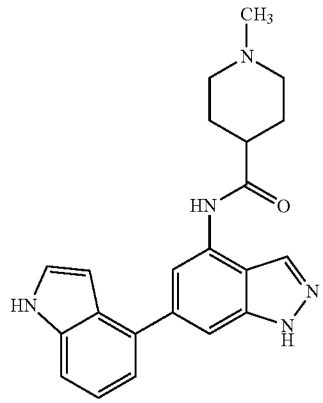 [SMILES: CN1CCC(C(=O)Nc2cc(-c3cccc4[nH]ccc34)cc3[nH]ncc23)CC1] | 1-methyl-4-piperidine carboxylic acid hydrochloride | 0.6 | 374 |
| 29 | N-[6-(1H-indol-4-yl)-1H-indazol-4-yl]-1-(methylsulfonyl)-4-piperidine-carboxamide | 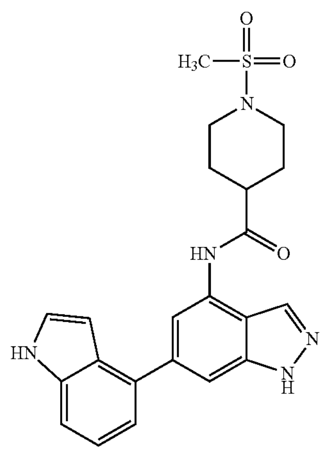 [SMILES: CS(=O)(=O)N1CCC(C(=O)Nc2cc(-c3cccc4[nH]ccc34)cc3[nH]ncc23)CC1] | 1-(methylsulfonyl)-4-piperidine-carboxylic acid (available from ABCR) | 0.85 | 438 |
| 30 | N-[6-(1H-indol-4-yl)-1H-indazol-4-yl]-5-oxo-3-pyrrolidine-carboxamide | 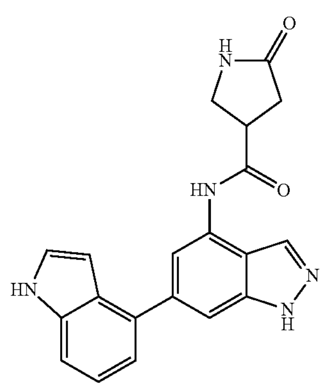 [SMILES: O=C1CC(C(=O)Nc2cc(-c3cccc4[nH]ccc34)cc3[nH]ncc23)CN1] | 5-oxo-3-pyrrolidine-carboxylic acid | 0.72 | 360 |

| Example Number | Name | Structure | Precursor acid | LCMS Rt (min) | MH+ |
|---|---|---|---|---|---|
| 31 | N-[6-(1H-indol-4-yl)-1H-indazol-4-yl]-1-(1-methylethyl)-5-oxo-3-pyrrolidine carboxamide | 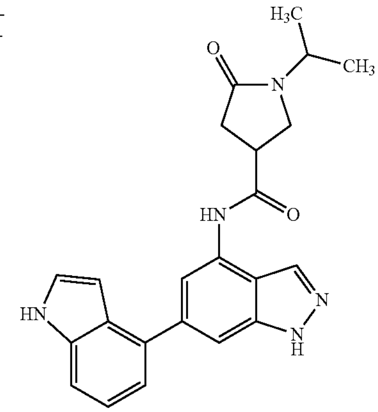 | 1-(1-methylethyl)-5-oxo-3-pyrrolidine-carboxylic acid | 0.83 | 402 |

Example 32

N-[6-(1H-Indol-4-yl)-1H-indazol-4-yl]cyclopropanecarboxamide

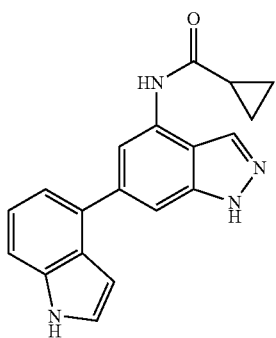 [SMILES: O=C(Nc1cc(-c2cccc3[nH]ccc23)cc2[nH]ncc12)C1CC1]

To a solution of 6-(1H-indol-4-yl)-2-(tetrahydro-2H-pyran-2-yl)-2H-indazol-4-amine (46 mg, 0.137 mmol) in DCM (1 ml) was added DIPEA (0.119 ml, 0.684 mmol) and cyclopropyl carbonyl chloride (29 mg, 0.274 mmol). The reaction was stirred at room temperature for 1 hour, then 2M sodium hydroxide solution (2 ml) was added and the reaction stirred at room temperature for a further 1 hour. The organic layer was collected by passing through a hydrophobic frit. The aqueous layer was washed several times with DCM. The organic extracts were combined and solvent removed by blow down. The residue was dissolved in methanol (2 ml) and 4M HCl in 1,4-dioxane added (2 ml). The reaction was stirred at room temperature for 1 hour. The solvent was removed by blow down and the residue purified by mass directed preparative HPLC (method B). The residue was freeze dried to give the title compound as a pale brown solid (9 mg).

LCMS (Method A) m/z 317 [MH+], $R_t$ 2.91 min.

| Example number | Name | Structure | Precursor Acid chloride | Rt (min) | MH+ |
|---|---|---|---|---|---|
| 33 | 3-(dimethylamino)-N-[6-(1H-indol-4-yl)-1H-indazol-4-yl]benzamide | 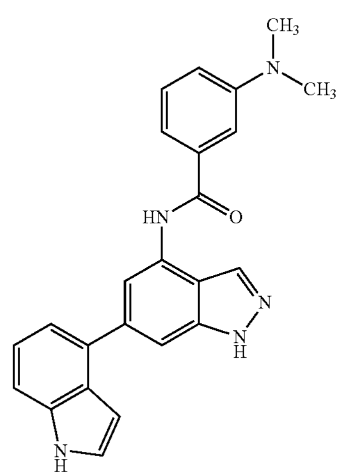 [SMILES: CN(C)c1cccc(C(=O)Nc2cc(-c3cccc4[nH]ccc34)cc3[nH]ncc23)c1] | | 3.23 | 396 |

| Example number | Name | Structure | Precursor Acid chloride | Rt (min) | MH+ |
|---|---|---|---|---|---|
| 34 | formic acid-4-amino-N-[6-(1H-indol-4-yl)-1H-indazol-4-yl]benzamide (1:1) | 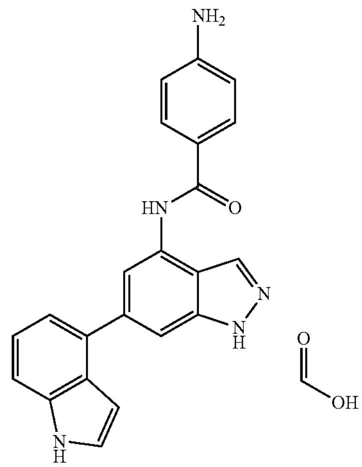 | | 2.85 | 368 |
| 35 | (1R,2R)-N-[6-(1H-indol-4-yl)-1H-indazol-4-yl]-2-phenyl-cyclopropane-carboxamide | 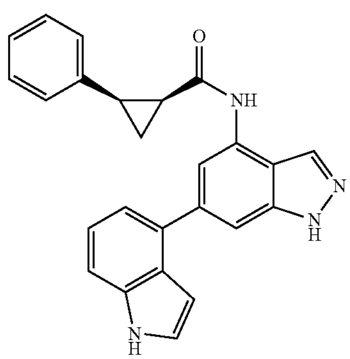 [SMILES: O=C(Nc1cc(-c2cccc3[nH]ccc23)cc2[nH]ncc12)[C@H]1C[C@H]1c1ccccc1] | | 3.4 | 393 |
| 36 | N-[6-(1H-indol-4-yl)-1H-indazol-4-yl]cyclohexane carboxamide | 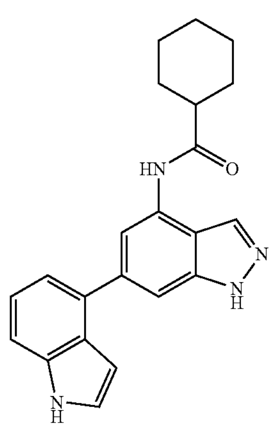 [SMILES: O=C(Nc1cc(-c2cccc3[nH]ccc23)cc2[nH]ncc12)C1CCCCC1] | | 3.28 | 359 |

Example 37

Phenylmethyl 3-hydroxy-4-({[6-(1H-indol-4-yl)-1H-indazol-4-yl]amino}carbonyl)-1-pyrrolidinecarboxylate

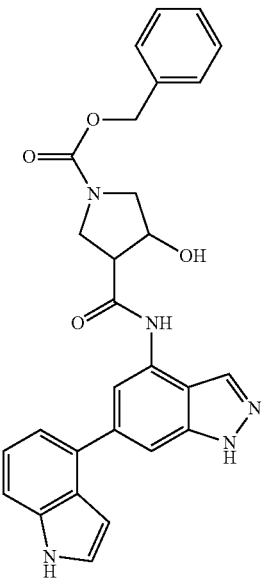 [SMILES: O=C(Nc1cc(-c2cccc3[nH]ccc23)cc2[nH]ncc12)C1CN(C(=O)OCc2ccccc2)CC1O]

To a solution of 4-hydroxy-1-{[(phenylmethyl)oxy]carbonyl}-3-pyrrolidinecarboxylic acid (available from Fluorochem, 59 mg, 0.22 mmol) in DMF (1 ml) was added HATU (85 mg, 0.22 mmol) and the mixture stirred for 10 mins. Then 6-(1H-indol-4-yl)-1H-indazol-4-amine (46 mg, 0.19 mmol) and DIPEA (0.065 ml, 0.37 mmol) were added and the mixture allowed to stand for 18 h at 20° C. The solvent was removed under a stream of nitrogen and the residue purified by Mass Directed Automated Preparative HPLC (Method E), to give the title compound (6 mg) as a brown solid.

LCMS (Method C) m/z 496 [MH$^+$], R$_t$=2.44 mins.

Biological Data
Determination of AKT Phosphorylation in Expanded T Cells Using Flow Cytometry
Assay Principle The assay measures the single cell phosphorylation of AKT in response to co stimulation of CD3/CD28 on expanded T cells with anti CD3 and anti CD28. Intracellular protein phosphorylation is analysed using a Beckman Coulter FC500 microplate loading (MPL) flow cytometer, after labelling with fluorochrome conjugated phospho protein specific antibodies. In this case intracellular phosphorylated AKT was labelled with monoclonal antibodies to phospho-AKT S473 directly conjugated to Alexa 488. Light scatter versus fluorescence scatter plots are made and AKT phosphorylation is detected as an increase in % of activated (pAKT) cells.

Assay Protocol
Cell Plating

Remove expanded T cells from flasks (See appendix below). Centrifuge and remove supernatant. Re-suspend pellet in warm (37 C) stimulation buffer (RPMI containing pen/strep/glutamine and 5% FCS) and centrifuge again. Re-suspend pellet in 10-20 mls of warm stimulation buffer and count. Adjust cell concentration to 1×10$^6$ cells/ml. Add 45 ul of cell suspension to wells of v bottomed polystyrene plates and incubate at 37 C for 90 minutes.

Prepare stimulant plate containing anti CD3 (BDBiosciences #555329) and anti CD28 (BD Biosiences #555725). Require 1-0.7 ug of each antibody per well. Stock antibody solutions are at 1000 ug/ml. Add an appropriate volume of diluted antibody solution to each well. Addition of 5 ul of this stock solution to cells results in a final concentration of 1-0.7 ug of each antibody per well.

Compound Plate Preparation and Stimulant Addition

Add serial (1/3) diluted compounds in wells A1-H10 (columns 11 and 12 contained stimulated and un-stimulated cells respectively). Top concentration is 10 uM and resulting final DMSO concentration is 0.15% DMSO. These steps are usually automated using a Beckman Coulter Biomek FX. Positive control is also included in plate sets (as a bundle). Positive control used in this assay is GW450853X (LY294002). Make up stock solutions of compounds at 6.66M and serially dilute it by 1 in 3 with 100% DMSO (8-span Biomek FX). Make plate replicates (stamp out) required number of plates. Each well contains 0.75 ul of compound at 6.666M in 100% DMSO (Use Biomek automation protocol). Dilute serially diluted stock compounds to 100 uM by adding 49.25 ul of stimulation buffer.

A further 1/10 dilution will result in a top concentration of 10 uM containing 0.15% DMSO. In this case 5 ul of each diluted compound is added to plates containing 50 ul of rested cell suspension. Columns 11 and 12 contain stimulation buffer and DMSO only.

Cell Treatments

Set up Biomek deck with compound plates and tip boxes as required. Place cell plates in appropriate deck locations on the Biomek FX. Start Biomek Program transfer 5 ul of each compound to cell plates. Following addition of compounds each plate is shaken gently (600 rpm) for 5 seconds. Once finished, place lids on plates and transfer them to a carbon dioxide incubator. Incubate in the presence of compound for 30 mins.

Cell Stimulation

Set up Biomek FX as per automation protocol. Place stimulation plate on deck. Place cell plates in position and add stimulant. Remove plates and place back in incubator for 19.25 minutes (total stimulation time is 20 mins)

Cell Fixation

Set up Biomek deck as per Cell fixation protocol. Pour pre warmed fixative (4% buffered paraformaldehyde solution or BD Cytofix reagent) into reservoir and place on heated deck (temperature maintained at 37 deg C.). Centrifuge plates for 5 mins at 1000 g. Remove fixative supernatant by pipetteing using Biomek FX. Break up pellets by vortexing wells. This is performed by simply sweeping the bottom on the plates over a whirlymixer. Arrange a large tray of ice (capable of holding several pates). Arrange plates on the ice and add 200 ul of ice-cold 90% methanol to each well. Cover and leave on ice for 30 minutes. Centrifuge plates at 1000 g for 5 minutes and remove methanol solution. Vortex plates and wash with 100 ul of PBS. Centrifuge again for 5 mins at 1000 g. Remove supernatant and vortex pellet Add 50 ul of Alexa fluor 488 Phospho-Akt (Ser 473) phospho specific rabbit monoclonal antibody (CST #2336) solution (1/100 dilution of stock anti body in stain solution). Cover plates and incubate in the dark for 60 minutes. Centrifuge plates (1000 g for 5 mins), remove supernatant and wash once using stain buffer. Re-suspend pellet in 180 ul of stain buffer (PBS, 2.5% FCS, 0.02% NaN3) Analyze plates using the FC500 MPL flow cytometer.

APPENDIX

T Cell Expansion
Coating of Tissue Culture Plates for Stimulation

Add 1.5 ml of PBS containing 1 mM MgCl2, 1 mM CaCl2, anti CD3 5 ug/ml and anti CD28 5 ug/ml to each well of 6 well Costar Tissue culture plate and incubate overnight at 37 deg C. in a CO2 incubator. This will coat the plate with the mAb's.

Wash the wells of the Costar plates once with 3 ml/well of PBS.

Re-suspend the PBMCs at $2\times10^6$ cells/ml in the growth media with IL-2 (10 ng/ml, R&D Systems #202-IL) and PHA (2 ug/ml, Sigma # L2769). Add 3 mls of the cell suspension to each well of a six well culture dish (Costar). Incubate the plate at 37 deg C. in a CO2 incubator until they are confluent i.e. the medium turns yellow.

After four days, wash the stimulated lymphocytes from culture wells using growth media. Culture lymphocytes in growth media (RPMI GIBCO CT 5615 10% Heat inactivated FCS, Hyclone, 2 mM Glutamine GIBCO, 1% Pen/Strep GIBCO, 1% Non essential amino acids, GIBCO, 1% Sodium Pyruvate, GIBCO, 20 uM Hepes GIBCO, 1.75 ul/500 mls 2-mercaptoethanol, Sigma]) in a medium size flask (T75) at a concentration of $\sim10^6$/ml with IL-2 (10 ng/ml) and IL-7 (1 ng/ml, R&D Systems #207-IL). Allow the cells to expand in resting phase at 37° C. in a CO2 incubator for 4-7 days. During this period of expansion, check cell growth every day and top up with 10 to 15 ml of resting media with IL-2 (10 ng/ml) and IL-7 (1 ng/ml) depending on how confluent the growth is. If required transfer cells to larger flask (T175). $1\times10^6$/ml cells are stained with Propidium Iodide and analysed by flow cytometry. Apoptotic cells are excluded from viable cell counts for subsequent experiments. Cells should be >80% viable for use.

PI3K Alpha, Beta, Delta and Gamma Assays
Assay Principle

The assay readout exploits the specific and high affinity binding of PIP3 to an isolated pleckstrin homology (PH) domain in the generation of a signal. Briefly, the PIP3 product is detected by displacement of biotinylated PIP3 from an energy transfer complex consisting of Europium (Eu)-labelled anti-GST monoclonal antibody, a GST-tagged PH domain, biotin-PIP3 and Streptavidin-APC. Excitation of Eu leads to a transfer of energy to APC and a sensitized fluorescence emission at 665 nm. PIP3 formed by PI3kinase activity competes for the binding site on the PH domain, resulting in a loss of energy transfer and a decrease in signal.

Assay Protocol

Solid compounds are typically plated with 0.1 µl of 100% DMSO in all wells (except column 6 and 18) of a 384-well, v bottom, low volume Greiner plate. The compounds are serially diluted (4-fold in 100% DMSO) across the plate from column 1 to column 12 and column 13 to column 24 and leave column 6 and 18 containing only DMSO to yield 11 concentrations for each test compound.

The assays are run using specific PI3 kinase kits from Millipore (Cat#33-001)

The assay kit consist of the following:
4×PI3K reaction buffer (Contains 200 mM Hepes pH 7, 600 mM NaCl, 40 mM Mgcl₂, <1% Cholate (w/v), <1% Chaps (w/v), 0.05% Sodium Azide (w/v))
PIP2 (1 mM)
3× Biotin PIP3 (50 µM)
Detection Mix C (Contains 267 mM KF)
Detection Mix A (Contains 60 µg/ml streptavadin-APC)
Detection Mix B (Contains 36 µg/ml Europium-anti-GST (Anti-GST-K) and 90 µg/ml GST-GRP1—PH-Domain and 1 mM DTT)
Stop Solution (Contains 150 mM EDTA)

Manually add 3 µl of Reaction buffer (contains 1 mM DTT) to column 18 only for 100% inhibition control (no activity)

Manually add 3 µl of 2× Enzyme solution to all wells except column 18. Preincubate with compound for 15 minutes.

Manually add 3 µl of 2× Substrate solution to all wells. (column 6 represents 0% inhibition control)

Leave plate for 1 hr (cover from light) (In the case of Gamma only a 50 min incubation is required)

Manually add 3 µl Stop/Detection solution to all wells
Leave plate for 1 hour (cover from light)

The assay is read upon the BMG Rubystar and the ratio data is utilised to calculate 11 point curves.

NB The substrate solution (concentrations) differ with each isoform (see below)

Alpha
2× substrate solution containing 500 µM ATP, 16 µM PIP2 and 0.030 µM 3× biotin-PIP3.

Beta
2× substrate solution containing 800 µM ATP, 16 µM PIP2 and 0.030 µM 3× biotin-PIP3.

Delta
2× substrate solution containing 160 µM ATP, 10 µM PIP2 and 0.030 µM 3× biotin-PIP3.

Gamma
2× substrate solution containing 30 µM ATP, 16 µM PIP2 and 0.030 µM 3× biotin-PIP3.

Analysis Method

Data processed through the XC50 4-parameter logistic curve fit algorithm in Activity Base.

Normalise to % inhibition between the high and low controls (0% and 100% inhibition respectively)

Primary Module fit: Slope, Min and Max asymptotes varies
Secondary Module fits: (1) Fix Min asymptote, (2) Fix Max asymptote, (3) Fix Min and Max asymptotes Curve Fit QC:pXC50 95% CL ratio>10
−20<Min asymptote<20
80<Max asymptote<120

The compounds of Examples 1 to 37 were tested in one or more of the PI3K Alpha, Beta, Delta and/or Gamma assays above or similar assays and were found to have a mean $pIC_{50}$ of 5 or greater. Certain compounds were also tested in the T cell assay above or a similar assay and were found to have a mean $pIC_{50}$ of 5 or greater.

What is claimed is:
1. A compound of formula (I):

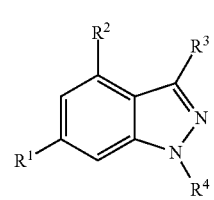

wherein
$R^1$ is 9- or 10-membered bicyclic heteroaryl wherein the 9- or 10-membered bicyclic heteroaryl contains from one to three heteroatoms independently selected from oxygen and nitrogen and is optionally substituted by $C_{1-6}$alkyl, $C_{3-6}$cycloalkyl, halo or —CN;

$R^2$ is —NHCOR$^5$, $R^3$ is hydrogen or fluoro;

$R^4$ is hydrogen or methyl;

$R^5$ is phenyl optionally substituted by one or two substituents independently selected from $C_{1-6}$alkyl, —OR$^{10}$, halo, —NR$^{11}$R$^{12}$, and phenyl optionally substituted by halo;

$R^{11}$ and $R^{12}$ are each independently hydrogen or $C_{1-6}$alkyl; and $R^{10}$ is $C_{1-6}$alkyl optionally substituted by from one to three fluoros;

or a salt thereof.

2. A compound according to claim 1 wherein $R^1$ is 9- or 10-membered bicyclic heteroaryl wherein the 9- or 10-membered bicyclic heteroaryl contains from one to three heteroatoms independently selected from oxygen and nitrogen.

3. A compound according to claim 1 wherein $R^1$ is indolyl.

4. A compound according to claim 1 wherein $R^3$ is hydrogen.

5. A compound according to claim 1 wherein $R^4$ is hydrogen.

6. A compound which is:

N-[6-(1H-indol-4-yl)-1H-indazol-4-yl]benzamide;
2-fluoro-N-[6-(1H-indol-4-yl)-1H-indazol-4-yl]benzamide;
2,3-difluoro-N-[6-(1H-indol-4-yl)-1H-indazol-4-yl]benzamide;
2,5-difluoro-N-[6-(1H-indol-4-yl)-1H-indazol-4-yl]benzamide;
N-[6-(1H-indol-4-yl)-1H-indazol-4-yl]-2-methylbenzamide;
2'-chloro-N-[6-(1H-indol-4-yl)-1H-indazol-4-yl]-2-biphenylcarboxamide;
2,4-difluoro-N-[6-(1H-indol-4-yl)-1H-indazol-4-yl]benzamide;
2,6-difluoro-N-[6-(1H-indol-4-yl)-1H-indazol-4-yl]benzamide;
N-[6-(1H-indol-4-yl)-1H-indazol-4-yl]-2-(methyloxy)benzamide;
2-[(difluoromethyl)oxy]-N-[6-(1H-indol-4-yl)-1H-indazol-4-yl]benzamide;
N-[6-(1H-indol-4-yl)-1H-indazol-4-yl]-4-methyl-2-(methyloxy)benzamide;
N-[6-(1H-indol-4-yl)-1H-indazol-4-yl]-5-methyl-2-(methyloxy)benzamide;
N-[6-(1H-indol-4-yl)-1H-indazol-4-yl]-3-methyl-2-(methyloxy)benzamide;
2-(ethyloxy)-N-[6-(1H-indol-4-yl)-1H-indazol-4-yl]benzamide;
N-[6-(1H-indol-4-yl)-1H-indazol-4-yl]-3-methylbenzamide;
3-(dimethylamino)-N-[6-(1H-indol-4-yl)-1H-indazol-4-yl]benzamide;
4-amino-N-[6-(1H-indol-4-yl)-1H-indazol-4-yl]benzamide;
or
a salt thereof.

7. A compound which is:

N-[6-(1H-indol-4-yl)-1H-indazol-4-yl]benzamide;
2-fluoro-N-[6-(1H-indol-4-yl)-1H-indazol-4-yl]benzamide;
2,3-difluoro-N-[6-(1H-indol-4-yl)-1H-indazol-4-yl]benzamide;
2,5-difluoro-N-[6-(1H-indol-4-yl)-1H-indazol-4-yl]benzamide;
N-[6-(1H-indol-4-yl)-1H-indazol-4-yl]-2-methylbenzamide;
2'-chloro-N-[6-(1H-indol-4-yl)-1H-indazol-4-yl]-2-biphenylcarboxamide;
2,4-difluoro-N-[6-(1H-indol-4-yl)-1H-indazol-4-yl]benzamide;
2,6-difluoro-N-[6-(1H-indol-4-yl)-1H-indazol-4-yl]benzamide;
N-[6-(1H-indol-4-yl)-1H-indazol-4-yl]-2-(methyloxy)benzamide;
2-[(difluoromethyl)oxy]-N-[6-(1H-indol-4-yl)-1H-indazol-4-yl]benzamide;
N-[6-(1H-indol-4-yl)-1H-indazol-4-yl]-4-methyl-2-(methyloxy)benzamide;
N-[6-(1H-indol-4-yl)-1H-indazol-4-yl]-5-methyl-2-(methyloxy)benzamide;
N-[6-(1H-indol-4-yl)-1H-indazol-4-yl]-3-methyl-2-(methyloxy)benzamide;
2-(ethyloxy)-N-[6-(1H-indol-4-yl)-1H-indazol-4-yl]benzamide;
N-[6-(1H-indol-4-yl)-1H-indazol-4-yl]-3-methylbenzamide;
3-(dimethylamino)-N-[6-(1H-indol-4-yl)-1H-indazol-4-yl]benzamide;
4-amino-N-[6-(1H-indol-4-yl)-1H-indazol-4-yl]benzamide;
or
a salt thereof.

8. A compound according to claim 1 in the form of a pharmaceutically acceptable salt thereof.

9. A pharmaceutical composition comprising a compound as defined in claim 1, or a pharmaceutically acceptable salt thereof, and one or more pharmaceutically acceptable excipients.

\* \* \* \* \*